US010421964B2

(12) United States Patent
Tachikawa et al.

(10) Patent No.: US 10,421,964 B2
(45) Date of Patent: *Sep. 24, 2019

(54) UNA OLIGOMERS AND COMPOSITIONS FOR TREATING AMYLOIDOSIS

(71) Applicant: Arcturus Therapeutics, Inc., San Diego, CA (US)

(72) Inventors: Kiyoshi Tachikawa, San Diego, CA (US); Joseph E. Payne, San Diego, CA (US); Padmanabh Chivukula, San Diego, CA (US)

(73) Assignee: ARCTURUS THERAPEUTICS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/876,127

(22) Filed: Jan. 20, 2018

(65) Prior Publication Data

US 2018/0148725 A1 May 31, 2018

Related U.S. Application Data

(63) Continuation of application No. PCT/US2016/043927, filed on Jul. 25, 2016, which is a continuation of application No. 14/807,223, filed on Jul. 23, 2015, now Pat. No. 9,856,475.

(51) Int. Cl.
| | | |
|---|---|---|
| *C12N 15/113* | (2010.01) | |
| *A61K 9/127* | (2006.01) | |
| *A61K 31/685* | (2006.01) | |
| *A61K 31/713* | (2006.01) | |
| *C12N 15/11* | (2006.01) | |
| *A61K 9/00* | (2006.01) | |

(52) U.S. Cl.
CPC ............ *C12N 15/113* (2013.01); *A61K 9/127* (2013.01); *A61K 31/685* (2013.01); *A61K 31/713* (2013.01); *C12N 15/111* (2013.01); *C12N 15/1138* (2013.01); *A61K 9/0019* (2013.01); *C12N 2310/14* (2013.01); *C12N 2310/315* (2013.01); *C12N 2310/32* (2013.01); *C12N 2310/321* (2013.01); *C12N 2310/322* (2013.01); *C12N 2310/323* (2013.01); *C12N 2310/3525* (2013.01); *C12N 2310/3533* (2013.01); *C12N 2320/32* (2013.01); *C12N 2320/34* (2013.01)

(58) Field of Classification Search
None
See application file for complete search history.

(56) References Cited

U.S. PATENT DOCUMENTS

| | | |
|---|---|---|
| 4,199,574 A | 4/1980 | Schaeffer |
| 4,968,686 A | 11/1990 | Townsend |
| 5,786,359 A | 7/1998 | Reitz |
| 5,898,031 A | 4/1999 | Crooke |
| 6,037,176 A | 3/2000 | Bennett |
| 6,069,132 A | 5/2000 | Revanker |
| 6,506,559 B1 | 1/2003 | Fire et al. |
| 6,608,035 B1 | 8/2003 | Agrawal |
| 6,753,139 B1 | 6/2004 | Baulcombe |
| 7,056,704 B2 | 6/2006 | Tuschl |
| 7,078,196 B2 | 7/2006 | Tuschl |
| 7,459,547 B2 | 12/2008 | Zamore et al. |
| 7,579,451 B2 | 8/2009 | Manoharan |
| 7,691,995 B2 | 4/2010 | Zamore |
| 7,745,608 B2 | 6/2010 | Manoharan |
| 7,750,144 B2 | 7/2010 | Zamore |
| 7,786,290 B2 | 8/2010 | Woppmann |
| 7,915,399 B2 | 3/2011 | MacLachlan |
| 8,101,584 B2 | 1/2012 | Kreutzer |
| 8,101,742 B2 | 1/2012 | Kreutzer |
| 8,258,285 B2 | 9/2012 | Baulcombe |
| 8,314,227 B2 | 11/2012 | Wengel |
| 8,362,231 B2 | 1/2013 | Tuschl |
| 8,420,391 B2 | 4/2013 | Tuschl |
| 8,546,143 B2 | 10/2013 | Kreutzer |
| 9,051,570 B2 | 6/2015 | Wengel |
| 9,365,610 B2 | 6/2016 | Payne |
| 9,856,475 B2* | 1/2018 | Tachikawa ............. A61K 9/127 |
| 9,982,259 B2* | 5/2018 | Tachikawa ............. A61K 9/127 |
| 2002/0086356 A1 | 7/2002 | Tuschl |
| 2003/0143732 A1 | 7/2003 | Fosnaugh |
| 2004/0171570 A1 | 9/2004 | Allerson |
| 2004/0175703 A1 | 9/2004 | Kreutzer et al. |
| 2004/0192626 A1 | 9/2004 | McSwiggen et al. |
| 2004/0259247 A1 | 12/2004 | Tuschl et al. |
| 2004/0261149 A1 | 12/2004 | Fauquet et al. |
| 2005/0100907 A1 | 5/2005 | Kreutzer |
| 2005/0107325 A1 | 5/2005 | Manoharan |
| 2005/0129778 A1 | 6/2005 | Mulye |
| 2005/0223427 A1 | 10/2005 | Khvorova |
| 2005/0244858 A1 | 11/2005 | Rossi et al. |
| 2005/0288244 A1 | 12/2005 | Manoharan |

(Continued)

FOREIGN PATENT DOCUMENTS

| | | |
|---|---|---|
| CA | 2003037909 | 5/2003 |
| GB | 9629336 | 9/1996 |

(Continued)

OTHER PUBLICATIONS

Vaish (Nucleic Acids Research (2011) vol. 39(5):1823-1832). (Year: 2011).*

(Continued)

*Primary Examiner* — J. E. Angell
(74) *Attorney, Agent, or Firm* — Mintz, Levin, Cohn, Ferris, Glovsky and Popeo, P.C.

(57) ABSTRACT

This invention encompasses compounds and compositions useful in methods for medical therapy, in general, for inhibiting expression of a TTR gene in a subject. The compounds have a first strand and a second strand, the monomers comprising UNA monomers and nucleic acid monomers, and the compounds are targeted to a sequence of a TTR gene.

16 Claims, 11 Drawing Sheets

Specification includes a Sequence Listing.

(56) References Cited

U.S. PATENT DOCUMENTS

| | | |
|---|---|---|
| 2006/0122391 A1 | 6/2006 | Babu |
| 2006/0276635 A1 | 12/2006 | McSwiggen |
| 2006/0287260 A1 | 12/2006 | Manoharan |
| 2007/0275914 A1 | 11/2007 | Manoharan |
| 2009/0093438 A1 | 4/2009 | McSwiggen |
| 2010/0120893 A1* | 5/2010 | Sah .................. C12N 15/111 514/44 A |
| 2011/0136233 A1 | 6/2011 | Quay et al. |
| 2011/0313020 A1 | 12/2011 | Templin et al. |
| 2012/0120893 A1 | 5/2012 | Baligh et al. |
| 2012/0225927 A1 | 9/2012 | Sah |
| 2013/0096289 A1 | 4/2013 | Wengel |
| 2013/0190383 A1 | 7/2013 | Vaish et al. |
| 2013/0281510 A1 | 10/2013 | Ando et al. |
| 2014/0275211 A1 | 9/2014 | Sah et al. |
| 2014/0315835 A1 | 10/2014 | Rajeev |
| 2015/0141678 A1 | 5/2015 | Payne |
| 2015/0307880 A1 | 10/2015 | Tachikawa |
| 2015/0307881 A1 | 10/2015 | Tachikawa et al. |

FOREIGN PATENT DOCUMENTS

| | | |
|---|---|---|
| WO | WO -1996029336 | 9/1996 |
| WO | WO-9908688 A1 | 2/1999 |
| WO | WO -1999008688 | 2/1999 |
| WO | WO-2003004602 A2 | 1/2003 |
| WO | WO-2003037909 A1 | 5/2003 |
| WO | WO-03070918 A2 | 8/2003 |
| WO | WO-03106477 A1 | 12/2003 |
| WO | WO-2004090105 A2 | 10/2004 |
| WO | WO-2004090108 A2 | 10/2004 |
| WO | WO-2004094595 A2 | 11/2004 |
| WO | WO-2004108897 A2 | 12/2004 |
| WO | WO-2005089268 A2 | 9/2005 |
| WO | WO-2005089287 A2 | 9/2005 |
| WO | WO-2005121372 A2 | 12/2005 |
| WO | WO-06085987 A2 | 8/2006 |
| WO | WO-2006112872 A2 | 10/2006 |
| WO | WO-2007022369 A2 | 2/2007 |
| WO | WO-2007051303 A1 | 5/2007 |
| WO | WO-2007056829 A1 | 5/2007 |
| WO | WO-2008020435 A2 | 2/2008 |
| WO | WO-08147824 A2 | 12/2008 |
| WO | WO-2011123468 A1 | 10/2011 |
| WO | WO-2011133584 A2 | 10/2011 |
| WO | WO-2014037436 A1 | 3/2014 |
| WO | WO-2015042564 A1 * | 3/2015 .......... C12N 15/113 |

OTHER PUBLICATIONS

2015/042564 Vaish et al. (Nucleic Acids Research, 2011, 39(5):1823-1832).

Bartlett, Effect of siRNA Nuclease Stability on the In Vitro and In Vivo Kinetics of siRNA-Mediated Gene Silencing, Biotechnology and Bioengineering, vol. 97, No. 4, Jul. 1, 2007.

Bramsen et al., Nucleic Acids Research 2009, vol. 37, No. 9, pp. 2867-2881, A large-scale chemical modification screen identifies design rules to generate siRNAs with high activity, high stability and low toxicity.

Bramsen, Jesper B., et al., "A screen of chemical modifications identifies position-specific modification by UNA to most potently reduce siRNA off-target effects." Nucleic acids research 38.17 (2010): 5761-5773.

Czauderna, Nucleic Acids Research, 2003, vol. 31 (11), 2705-2716.

Elbashir, EMBO Journal, 2001, vol. 20 (23), 6877-6888.

Habus, Nucleosides & Nucleotides, 1995, vol. 14 (9&10), 1853-1859.

International Search Report; dated Mar. 11, 2009; 6 pages; International Application No. PCT/US2008/064417; International Filing Date: May 21, 2008; Applicant: Nastech Pharmaceutical Company Inc.; Title: Hydroxymethyl Substituted RNAOligonucleotides and RNA Complexes.

Jensen, T. et al.; "Unlocked Nucleic Acid (UNA) and UNA Derivatives: Thermal Denaturation Studies," Nucleic Acids Symposium Series No. 52; Oxford University Press 2008; pp. 133-134.

John Wiley & Sons, Inc.; "IUPAC-IUB Joint Commission on Biochemical Nomenclature Abbreviations and Symbols for the Description of Conformations of Polynucleotide Chains;" Current Protocols in Nucleic Acid Chemistry 2000; pp. A.1C.1-A.1D.3.

Layzer, In vivo activity of nuclease-resistant siRNAs, RNA (2004), vol. 10, pp. 766-771.

Mangos, M. et al.; "Efficient RNase H-Directed Cleavage of RNA Promoted by Antisense DNA or 2'F-ANA Constructs Containing Acyclic Nucleotide Inserts," Journal of the Amerian Chemical Society 2003; vol. 125; pp. 654-661.

Mangos, M. et al.; "Efficient RNase H-Directed Cleavage of RNA Promoted by Antisense DNA or 2'F-ANA Constructs Containing Acyclic Nucleotide Inserts;" Journal of the American Chemical Society 2003; vol. 125; pp. 654-661.

Nielsen, Oligonucleotide Analogues Containing 4'-C-(Hydroxymethyl)uridine: Synthesis, Evaluation and Mass Spectrometric Analysis, Bioorganic & Medicinal Chemistry, vol. 3, No. 1 I, pp. 1493-1502, 1995.

Nielsen, P. et al.; "Synthesis and Evaluation of Oligodeoxynucleotides Containing Acyclic Nucleosides: Introduction of Three Novel Analogues and a Summary;" Bioorganic & Medicinal Chemistry; Elsevier Science Ltd 1995; vol. 3; No. 1; pp. 19-28.

Pandolfi, Nucleosides & Nucleotides, 1999, vol. 18 (9), 2051-2069.

Pei et al, Arch Pharm Res 2009, vol. 31, No. 7, pp. 843-849, Synthesis of 3'-C-Hydroxymethyl-substituted Pyrimidine and Purine Nucleosides as Potential Anti-Hepatitis C Virus (HCV) Agents.

Petersen, LNA: A versatile tool for therapeutics and genomics, TRENDS in Biotechnology vol. 21 No. 2 Feb. 2003.

Pfundheller, Locked Nucleic Acid Synthesis, Chapter 8 in Methods in Molecular Biology, vol. 288: Oligonucleotide Synthesis: Methods and Applications, Edited by: P. Herdewijn, Humana Press, 2005.

pharmabiz.com, Arcturus to present gene knockdown data in non-human primates, showing up to 94% reduction in gene expression with single low dose, dated Oct. 14, 2014.

Snead, Nicholas M., et al., "5' Unlocked nucleic acid modification improves siRNA targeting." Molecular Therapy-Nucleic Acids 2 (2013): 7 Pages.

Thrane, H. et al.; "Novel Linear and Branched Oligodeoxynucleotide Analogues Containing 4'-C-(Hydroxymethyl Thymidine;" Tetrahedron; Elsevier Science Ltd 1995; vol. 51; No. 37; pp. 10389-10402.

Vaish, Narendra, et al., "Improved specificity of gene silencing by siRNAs containing unlocked nucleobase analogs." Nucleic acids research 39.5 (2010): 1823-1832.

Laursen, Maria B., et al., "Utilization of unlocked nucleic acid (UNA) to enhance siRNA performance in vitro and in vivo." Molecular BioSystems 6.5 (2010): 862-870.

* cited by examiner

SEQ ID NOS: 23-38

V30M TTR mRNA
3'-304-UCGGAAAGACUUGUGUACGUACCGGUGUAACUACCGUCCUG-264
3'-304-UCGGAAAGACUUGUGUACGUGCCGGUGUAACUACCGUCCUG-264
wt TTR mRNA

284

V30V-P2:  ACGGCCACAUUGAUGGCAGdTdT
V30V-P3:  CACGGCCACAUUGAUGGCAdTdT
V30V-P4:  GCACGGCCACAUUGAUGGCdTdT
V30V-P5:  UGCACGGCCACAUUGAUGGdTdT
V30V-P6:  AUGCACGGCCACAUUGAUGdTdT
V30V-P7:  CAUGCACGGCCACAUUGAUdTdT
V30V-P8:  ACAUGCACGGCCACAUUGAdTdT
V30V-P9:  CACAUGCACGGCCACAUUGdTdT
V30V-P10: ACACAUGCACGGCCACAUUdTdT
V30V-P11: AACACAUGCACGGCCACAUdTdT
V30V-P12: GAACACAUGCACGGCCACAdTdT
V30V-P13: UGAACACAUGCACGGCCACdTdT
V30V-P14: CUGAACACAUGCACGGCCAdTdT
V30V-P15: UCUGAACACAUGCACGGCCdTdT

FIG. 1

284 SEQ ID NOS: 39-48

```
V30M TTR mRNA
3'- 304-UCGGAAAGACUUGUGUACGUACCGGUGUAACUACCGUCCUG-264
3'- 304-UCGGAAAGACUUGUGUACGUGCCGGUGUAACUACCGUCCUG-264
wt TTR mRNA
        V30V-P5 :  UGCACGGCCACAUUGAUGGdTdT
        V30V-P9 :  CACAUGCACGGCCACAUUGdTdT
       V30V-P14 :  CUGAACACACAUGCACGGCCAdTdT
       V30V-P15 :  UCUGAACACACAUGCACGGCCdTdT
        V30M-P5 :  UGCAUGGCCACAUUGAUGGdTdT
        V30M-P9 :  CACAUGCAUGGCCACAUUGdTdT
       V30M-P14 :  CUGAACACAUGCAUGGCCAdTdT
       V30M-P15 :  UCUGAACACAUGCAUGGCCdTdT
```

FIG. 3

| siRNA ID | SS ID | SEQ ID NOS: 49-54 seq. (5' -> 3') | AS ID | SEQ ID NOS: 55-60 seq. (5' -> 3') |
|---|---|---|---|---|
| P15 | P15SS | GGCCAUGCAUGUGUUCAGAdTdT | P15AS | UCUGAACACAUGCAUGGCCdTdT |
| P15U6 | P15USS | ĞGCCAUGCAUGUGUUCAGAÜmU | P15U6AS | UCUGAĂCACAUGCAUGGCCÜmU |
| P15U7 | P15USS | ĞGCCAUGCAUGUGUUCAGAÜmU | P15U7AS | UCUGAAĈACAUGCAUGGCCÜmU |
| P15U14 | P15USS | ĞGCCAUGCAUGUGUUCAGAÜmU | P15U14AS | UCUGAACACAUGCĂUGGCCÜmU |
| P15U15 | P15USS | ĞGCCAUGCAUGUGUUCAGAÜmU | P15U15AS | UCUGAACACAUGCAŬGGCCÜmU |
| P15U16 | P15USS | ĞGCCAUGCAUGUGUUCAGAÜmU | P15U16AS | UCUGAACACAUGCAUĞGCCÜmU |

FIG. 6

| siRNA ID | SS ID | seq. (5' -> 3') | AS ID | seq. (5' -> 3') |
|---|---|---|---|---|
| P16 | P16SS | GCCAUGCAUGUGUUCAGAAdTdT | P16AS | UUCUGAACACAUGCAUGGCdTdT |
| P16U6 | P16USS | ĞCCAUGCAUGUGUUCAGAAŪmU | P16U6AS | UUCUGĀACACAUGCAUGGCŪmU |
| P16U7 | P16USS | ĞCCAUGCAUGUGUUCAGAAŪmU | P16U7AS | UUCUGAĀCACAUGCAUGGCŪmU |
| P16U15 | P16USS | ĞCCAUGCAUGUGUUCAGAAŪmU | P16U15AS | UUCUGAACACAUGCĀUGGCŪmU |
| P16U16 | P16USS | ĞCCAUGCAUGUGUUCAGAAŪmU | P16U16AS | UUCUGAACACAUGCAŪGGCŪmU |
| P16U17 | P16USS | ĞCCAUGCAUGUGUUCAGAAŪmU | P16U17AS | UUCUGAACACAUGCAUĞGCŪmU |

SEQ ID NOS: 61-66          SEQ ID NOS: 67-72

FIG. 8

UNA OLIGOMERS AND COMPOSITIONS FOR TREATING AMYLOIDOSIS

REFERENCE TO THE SEQUENCE LISTING

This application includes a Sequence Listing submitted electronically as an ASCII file created on Jan. 20, 2018, named ARC1242US_SL.txt, which is 37,860 bytes in size, and is hereby incorporated by reference in its entirety.

BACKGROUND OF THE INVENTION

The presence of certain diseases appears to correlate with expression of a mutant allele. For example, amyloidosis can be correlated to certain transthyretin (TTR) mutations. In such cases, it is desirable to selectively silence expression of the mutant allele, while maintaining expression of the wild-type variant.

Amyloidosis related to transthyretin (ATTR) involves the depositing of amyloid fibril proteins in various organs and tissues, including the peripheral, autonomic, and central nervous systems. Transthyretin (TTR) is a secreted thyroid hormone-binding protein that binds and transports retinol binding protein, and serum thyroxine in plasma and cerebrospinal fluid.

The pathology of ATTR may include many TTR mutations. Symptoms of ATTR often include neuropathy and/or cardiomyopathy. Peripheral neuropathy can begin in the lower extremities, with sensory and motor neuropathy, and can progress to the upper extremities. Autonomic neuropathy can be manifest by gastrointestinal symptoms and orthostatic hypotension.

Patients with TTR gene Val-30-Met, the most common mutation, have normal echocardiograms. However, they may have conduction system irregularities and need a pacemaker. The ATTR V30M variant can cause lower extremity weakness, pain, and impaired sensation, as well as autonomic dysfunction. Vitreous and opaque amyloid deposits can be characteristic of ATTR.

Survival upon onset of ATTR may be from five to fifteen years. The major treatment for ATTR amyloidosis is liver transplantation, which removes the major source of variant TTR production and replaces it with normal TTR. Liver transplantation slows disease progression and some improvement in autonomic and peripheral neuropathy can occur.

There is currently no pharmacological therapy that can undo the formation of TTR amyloid.

There is a continuing need for therapeutics for ATTR and other amyloid-related diseases.

There is a long-standing need for gene silencing agents that can selectively downregulate a disease-related allele.

There is also a need for active agents that can provide efficient and specific knockdown of TTR.

BRIEF SUMMARY

This invention relates to the fields of biopharmaceuticals and therapeutics that are operable by gene silencing. More particularly, this invention relates to the structures, compositions and uses of active agents for inhibiting expression of a TTR gene in a subject. The active agents are UNA oligomers that can be used for gene silencing, and among other things, in methods for treating transthyretin-related amyloidosis.

This invention relates to the fields of biopharmaceuticals and therapeutics based on allele selective gene silencing.

More particularly, this invention relates to methods for treating transthyretin-related amyloidosis with UNA oligomers capable of allele-selective knockdown of transthyretin.

This invention provides UNA oligomers for selectively inhibiting V30M TTR expression, which can be used in treating amyloidosis. The UNA oligomers can have a first strand and a second strand, each of the strands being 19-29 monomers in length, the monomers being UNA monomers and nucleic acid monomers. Embodiments include pharmaceutical compositions and methods for treating or preventing TTR-related amyloidosis by administering a UNA oligomer to a subject.

Embodiments of this invention include the following:

A UNA oligomer for selectively inhibiting V30M TTR expression, the oligomer comprising a first strand and a second strand, each of the strands being 19-29 monomers in length, the monomers comprising UNA monomers and nucleic acid monomers, wherein the oligomer has a duplex structure of from 14 to 29 monomers in length.

The UNA oligomer above, wherein the second strand has at least one UNA monomer in the duplex region. The UNA oligomer above, wherein the at least one UNA monomer in the second strand is at any one of positions 2-8 from the 5' end. The UNA oligomer above, wherein the at least one UNA monomer in the second strand is at any one of positions 9-18 from the 5' end. The UNA oligomer above, wherein the at least one UNA monomer in the second strand is at position 6, 7, 15, 16 or 17 from the 5' end.

The UNA oligomer above, wherein the oligomer has an IC50 for reducing V30M TTR expression of less than 20 pM.

The UNA oligomer above, wherein the oligomer has a selectivity ratio of at least 10, wherein the selectivity ratio is the ratio of the IC50 for reducing wild type TTR expression to the IC50 for reducing V30M TTR expression. The UNA oligomer above, wherein the oligomer has a selectivity ratio of at least 20. The UNA oligomer above, wherein the oligomer has a selectivity ratio in vitro of at least 50.

The UNA oligomer above, wherein the oligomer selectively inhibits V30M TTR expression in vivo. The UNA oligomer above, wherein the oligomer selectively inhibits V30M TTR expression ex vivo.

The UNA oligomer above, comprising at least one nucleic acid monomer that is base-modified, sugar-modified, or linkage modified.

A compound comprising a first strand and a second strand, each of the strands being 19-29 monomers in length, the monomers comprising UNA monomers and nucleic acid monomers, wherein the compound has a duplex region of from 14 to 29 contiguous monomers in length, wherein the first strand is a passenger strand for RNA interference and the second strand is a guide strand for RNA interference, and wherein the compound comprises a sequence of bases targeted to inhibit expression of a TTR gene. In some embodiments, the compound may contain from one to seven UNA monomers.

In certain embodiments, the compound may contain a UNA monomer at the 1-end (5' end for non-UNA) of the first strand, a UNA monomer at the second position from the 3' end of the first strand, and a UNA monomer at the second position from the 3' end of the second strand.

In further embodiments, the compound may contain a UNA monomer at any one or more of positions 2 to 8 from the 5' end of the second strand.

In additional embodiments, the compound may have a 3' overhang comprising one or more UNA monomers, natural nucleotides, non-natural nucleotides, modified nucleotides, or chemically-modified nucleotides, or combinations thereof. The compound may have a 3' overhang comprising one or more deoxythymidine nucleotides, 2'-O-methyl nucleotides, inverted abasic monomers, inverted thymidine monomers, L-thymidine monomers, or glyceryl nucleotides.

Embodiments of this invention contemplate compounds in which one or more of the nucleic acid monomers may be a non-natural nucleotide, a modified nucleotide, or a chemically-modified nucleotide. A nucleic acid monomer may have a 2'-O-methyl group, a 2'-methoxyethoxy, or a 2'-deoxy-2'-fluoro ribonucleotide.

In some embodiments, the compound may not contain fluorine.

A compound may have one or more of three monomers at each end of each strand being connected by a phosphorothioate, a chiral phosphorothioate, or a phosphorodithioate linkage.

This invention further contemplates a lipid nanoparticle-oligomer compound comprising one or more compounds above attached to the lipid nanoparticle, as well as compositions containing one or more compounds above and a pharmaceutically acceptable carrier. In certain embodiments, the carrier may include lipid nanoparticles or liposomes.

A composition of this disclosure, upon administering a single intravenous dose to a subject, may reduce TTR protein in the subject by at least 80% after 10 days, or at least 70% after 20 days, or at least 50% after 30 days.

Embodiments of this invention further include methods for treating or preventing TTR-related amyloidosis in a subject in need, by administering to the subject an effective amount of a composition above to the subject. The TTR-related amyloidosis can be ATTR. The administering can be intravenous, subcutaneous, pulmonary, intramuscular, intraperitoneal, or dermal. The effective amount can be a dose of from 0.001 to 10.0 mg/kg.

In some embodiments, upon administering a single dose to a subject, the composition may reduce TTR protein in the subject by at least 70% after 20 days, or by at least 50% after 30 days.

This invention includes methods for inhibiting expression of a TTR gene in a subject, by administering to the subject a composition above. Further aspects include the use of a composition above for preventing, ameliorating or treating a disease or condition associated with TTR-related amyloidosis in a subject in need, or for use in medical therapy, or for use in the treatment of the human or animal body.

This invention further includes compositions above for use in preparing or manufacturing a medicament for preventing, ameliorating or treating a disease or condition associated with TTR-related amyloidosis in a subject in need.

BRIEF DESCRIPTION OF THE DRAWINGS

FIG. 1 shows the single nucleotide polymorph (SNP) that exists at position 284 in the V30M mutation mRNA, as compared to the wild type (WT) TTR mRNA. Conventional siRNAs that are complementary to the WT mRNA can be tiled around position 284.

FIG. 3 shows that conventional siRNAs that are complementary to the V30M mRNA can be tiled around position 284. Four conventional siRNA variations, namely V30M-P5, V30M-P9, V30M-P14, and V30M-P15, were prepared. Also, as shown in FIG. 3, two reporter variants, V30V and V30M, each bearing nucleotide sequence 264 to 304 of human TTR, V30V being without the point mutation at position 284, and V30M containing the point mutation at position 284, were prepared and used in the PSICHECK reporter system in the 3'-UTR region of Luciferase gene.

FIG. 6 shows the structure of UNA oligomers that were effective in silencing V30M TTR, as measured in the PSI-CHECK reporter assay. Each of the UNA oligomer embodiments, P15U6, P15U7, P15U14, P15U15, and P15U16, contained four UNA monomers. In each UNA oligomer, a first UNA monomer was located at the 5' end of the first strand, also called the passenger strand. In each UNA oligomer, the second strand, also called the guide strand, formed a duplex region of 19 monomers length with the first strand. Each UNA oligomer had a duplex region of 19 monomers, and a two-monomer overhang at each end. In each UNA oligomer, a second UNA monomer was located at the 3' end of the first strand, in the $20^{th}$ position, which is in an overhang portion. In each UNA oligomer, a third UNA monomer was located at the 3' end of the second strand, in the $20^{th}$ position, which is in an overhang portion. In the UNA oligomer embodiments, P15U6, P15U7, P15U14, P15U15, and P15U16, a fourth UNA monomer was located in the second strand at positions 6, 7, 14, 15 and 16, respectively, counting from the 5' end of the second strand.

FIG. 7 shows the surprising and unexpected result that the selectivity of the UNA oligomers, P15U6, P15U7, P15U15, and P15U16, against V30M over V30V was substantially greater than for the conventional siRNA V30M-P15. In particular, the selectivity of UNA oligomer P15U6 against V30M over V30V was 24, meaning that the IC50 of UNA oligomer P15U6 against V30M (37.6 pM) was 24 times lower than the IC50 of UNA oligomer P15U6 against V30V (919.9 pM). This selectivity was advantageously 4-fold superior to the selectivity of 5.6 shown above in FIG. 5 for the conventional siRNA.

FIG. 8 shows the structure of UNA oligomers that were effective in silencing V30M TTR, as measured in the PSI-CHECK reporter assay. Each of the UNA oligomer embodiments, P16U6, P16U7, P16U15, P16U16, and P16U17, contained four UNA monomers. In each UNA oligomer, a first UNA monomer was located at the 5' end of the first strand, also called the passenger strand. In each UNA oligomer, the second strand, also called the guide strand, formed a duplex region of 19 monomers length with the first strand. Each UNA oligomer had a duplex region of 19 monomers, and a two-monomer overhang at each end. In each UNA oligomer, a second UNA monomer was located at the 3' end of the first strand, in the $20^{th}$ position, which is in an overhang portion. In each UNA oligomer, a third UNA monomer was located at the 3' end of the second strand, in the $20^{th}$ position, which is in an overhang portion. In the UNA oligomer embodiments, P16U6, P16U7, P16U15, P16U16, and P16U17, a fourth UNA monomer was located in the second strand at positions 6, 7, 15, 16 and 17, respectively, counting from the 5' end of the second strand.

FIG. 9 shows the surprising and unexpected result that the selectivity of the UNA oligomers, P16U6, P16U7, P16U15, and P16U16, against V30M over V30V was substantially greater than for the conventional siRNA V30M-P16. In particular, the selectivity of UNA oligomer P16U6 against V30M over V30V was 23, meaning that the IC50 of UNA oligomer P16U6 against V30M (92.4 pM) was 23 times lower than the IC50 of UNA oligomer P16U6 against V30V (2119 pM). This selectivity was advantageously 4-fold superior to the selectivity of 5.6 shown above in FIG. 5 for the conventional siRNA.

FIG. 10 (right) shows the surprising and unexpected result that the IC50 of UNA oligomer P16U6 against V30M (92.4 pM) was 23 times lower than the IC50 of UNA oligomer P16U6 against V30V (2119 pM). This selectivity was advantageously 4-fold superior to the selectivity of 5.6 shown above in FIG. 5 for the conventional siRNA.

DETAILED DESCRIPTION OF THE INVENTION

Figure 2:
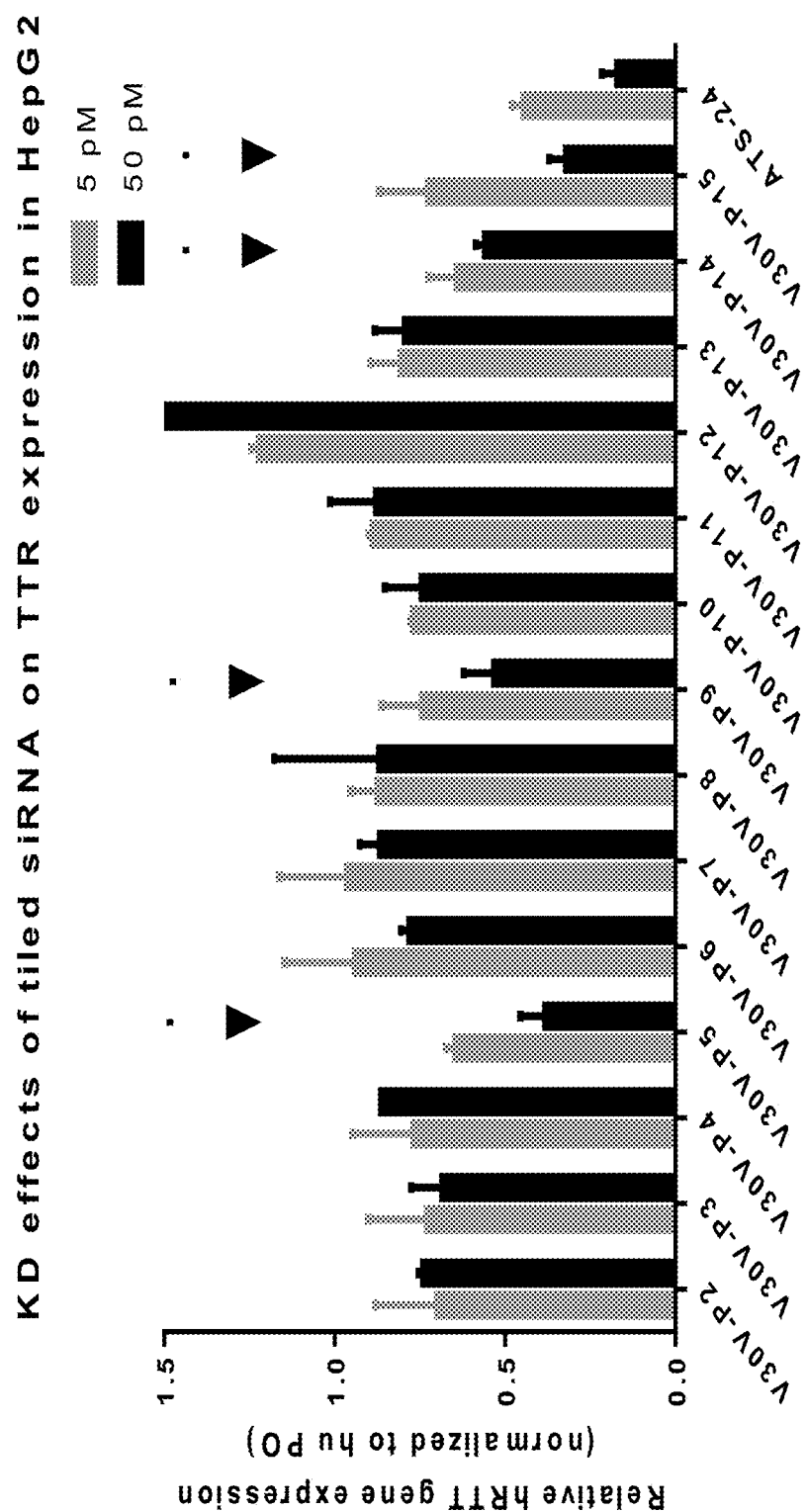
FIG. 2 shows that the conventional siRNAs complementary to the WT mRNA have limited activity in silencing the WT TTR gene, as measured by TTR knockdown in HepG2 cells. Positions 5, 9, 14 and 15, indicated by arrows, appear to be more accessible to silencing than other positions.

This invention provides UNA oligomers for selectively inhibiting V30M TTR expression. The UNA oligomers of this invention can be used as therapeutics for treating amyloidosis. In particular, this invention provides UNA oligomers, compositions and methods for treating transthyretin-related amyloidosis.

The UNA oligomers can have a first strand and a second strand, each of the strands being 19-29 monomers in length, the monomers being UNA monomers and nucleic acid monomers. Embodiments of this invention include compositions and methods for treating or preventing TTR-related amyloidosis by administering a UNA oligomer to a subject.

The UNA oligomers of this invention are capable of allele-specific knockdown of transthyretin.

In some embodiments, UNA oligomers are provided for treating amyloidosis related to transthyretin (ATTR). The UNA oligomers of this invention can reduce the depositing of amyloid fibril proteins in various organs and tissues, including the peripheral, autonomic, and central nervous systems.

In certain aspects, this invention provides therapeutics for ATTR and related amyloid-related diseases.

Aspects of this invention include UNA oligomers that can be used for treating clinical features of ATTR amyloidosis, including neuropathy and/or cardiomyopathy.

In some embodiments, UNA oligomers of this invention are targeted to one mutation Val-30-Met TTR.

This invention can provide a pharmacological therapy that can undo the formation of TTR amyloid.

*Homo sapiens* transthyretin (TTR) mRNA is found at NCBI Reference Sequence: NM_000371.3.

In some aspects, a composition of this invention can provide an unexpectedly advantageous duration of action. In certain embodiments, upon administering a single dose of a composition containing a UNA oligomer of this invention, the TTR protein in a subject may be reduced by at least 90% after 20 days.

In further embodiments, upon administering a single dose of a pharmaceutical composition containing a UNA oligomer of this invention, the TTR protein in a subject may be reduced by at least 70% for a period of at least 20 days.

In additional embodiments, upon administering a single dose of a pharmaceutical composition containing a UNA oligomer of this invention, the TTR protein in a subject may be reduced by at least 50% for a period of at least 30 days.

A subject can be a primate, a human, or other mammal.

UNA Oligomers

The UNA oligomers of this invention can be used for inhibiting V30M TTR expression.

A UNA oligomer of this invention the oligomer may have a first strand and a second strand, each of the strands being 19-29 monomers in length.

The monomers of a UNA oligomer can include UNA monomers and nucleic acid monomers A UNA oligomer can be a duplex structure of from 14 to 29 monomers in length.

In some embodiments, the second strand of a UNA oligomer can have at least one UNA monomer in the duplex region. In certain embodiments, a UNA oligomer can have at least one UNA monomer in the second strand at any of positions 6, 7, 15, 16 or 17 from the 5' end in the duplex region.

A UNA oligomer of this invention may have any number of UNA monomers within its total length.

A UNA oligomer can include a nucleic acid monomer that is base-modified, sugar-modified, or linkage modified.

Embodiments of this invention further provide UNA oligomers that selectively inhibit V30M TTR expression.

In certain embodiments, a UNA oligomer has an IC50 for reducing V30M TTR expression in vitro of less than 20 pM.

In further embodiments, a UNA oligomer can have a selectivity ratio in vitro of at least 5. The selectivity ratio is the ratio of the IC50 for reducing V30M TTR expression to the IC50 for reducing wild type TTR expression. The selectivity ratio of a UNA oligomer of this invention can range from 2 to 1000. In certain embodiments, the selectivity ratio of a UNA oligomer is at least 2, or at least 5, or at least 10, or at least 30, or at least 30, or at least 50, or at least 100.

In some aspects, a UNA oligomer of this invention can selectively inhibit V30M TTR expression in vivo.

In certain aspects, a UNA oligomer of this invention can selectively inhibit V30M TTR expression ex vivo.

A UNA oligomer can be an active pharmaceutical molecule being a chain composed of monomers, also called an oligomer. The monomers of the oligomer can include UNA monomers and other nucleic acid monomers.

The UNA monomers are novel, synthetic molecules that can be attached in a chain to form an oligomer.

The nucleic acid monomers can be naturally-occurring nucleotides, modified naturally-occurring nucleotides, or certain non-naturally-occurring nucleotides.

A UNA oligomer of this invention is a synthetic, pharmacologically active molecule and can be used in the treatment of a condition or disease.

A UNA oligomer of this disclosure can be a double stranded oligomer. Each strand of the double stranded oligomer can be composed of UNA monomers along with a number of nucleic acid monomers for a total length of 19 to 29 monomers.

A UNA oligomer of this invention can contain one or more UNA monomers in any strand. The UNA monomers can be in a single strand, or in either strand of a double stranded UNA oligomer, or in both strands of a double stranded UNA oligomer.

UNA Monomers

In some embodiments, linker group monomers can be unlocked nucleomonomers (UNA monomers), which are small organic molecules based on a propane-1,2,3-tri-yl-trisoxy structure as shown below:

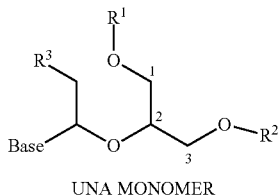

UNA MONOMER where $R^1$ and $R^2$ are H, and $R^1$ and $R^2$ can be phosphodiester linkages, Base can be a nucleobase, and $R^3$ is a functional group described below.

In another view, the UNA monomer main atoms can be drawn in IUPAC notation as follows:

UNA monomer unit

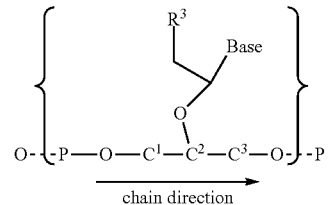

chain direction where the direction of progress of the oligomer chain is from the 1-end to the 3-end of the propane residue.

Examples of a nucleobase include uracil, thymine, cytosine, 5-methylcytosine, adenine, guanine, inosine, and natural and non-natural nucleobase analogues.

In general, because the UNA monomers are not nucleotides, they can exhibit at least four forms in an oligomer. First, a UNA monomer can be an internal monomer in an oligomer, where the UNA monomer is flanked by other monomers on both sides. In this form, the UNA monomer can participate in base pairing when the oligomer is a duplex, for example, and there are other monomers with nucleobases in the duplex.

Examples of UNA monomer as internal monomers flanked at both the propane-1-yl position and the propane-3-yl position, where $R^3$ is —OH, are shown below.

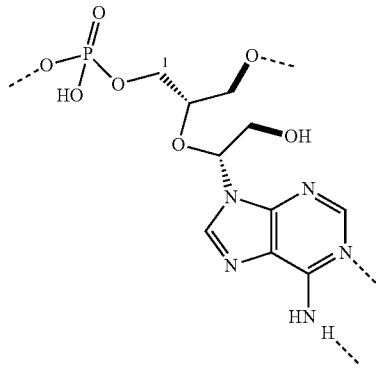

UNA-A

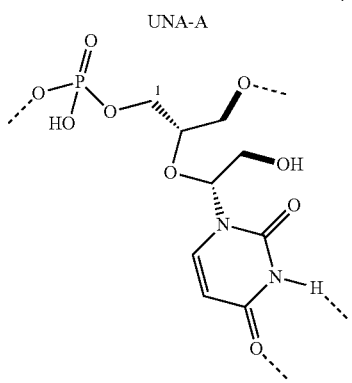

UNA-U

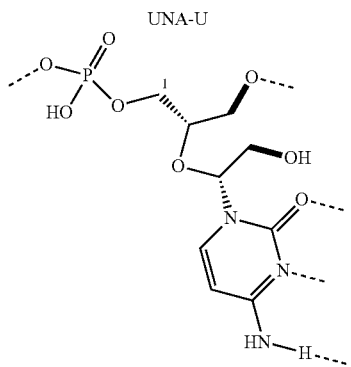

UNA-C

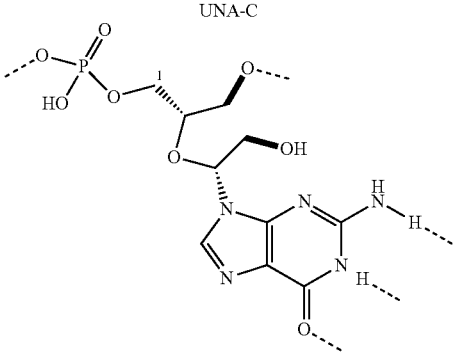

UNA-G

Second, a UNA monomer can be a monomer in an overhang of an oligomer duplex, where the UNA monomer is flanked by other monomers on both sides. In this form, the UNA monomer does not participate in base pairing. Because the UNA monomers are flexible organic structures, unlike nucleotides, the overhang containing a UNA monomer will be a flexible terminator for the oligomer.

A UNA monomer can be a terminal monomer in an overhang of an oligomer, where the UNA monomer is attached to only one monomer at either the propane-1-yl position or the propane-3-yl position. In this form, the UNA monomer does not participate in base pairing. Because the UNA monomers are flexible organic structures, unlike nucleotides, the overhang containing a UNA monomer can be a flexible terminator for the oligomer.

Examples of a UNA monomer as a terminal monomer attached at the propane-3-yl position are shown below.

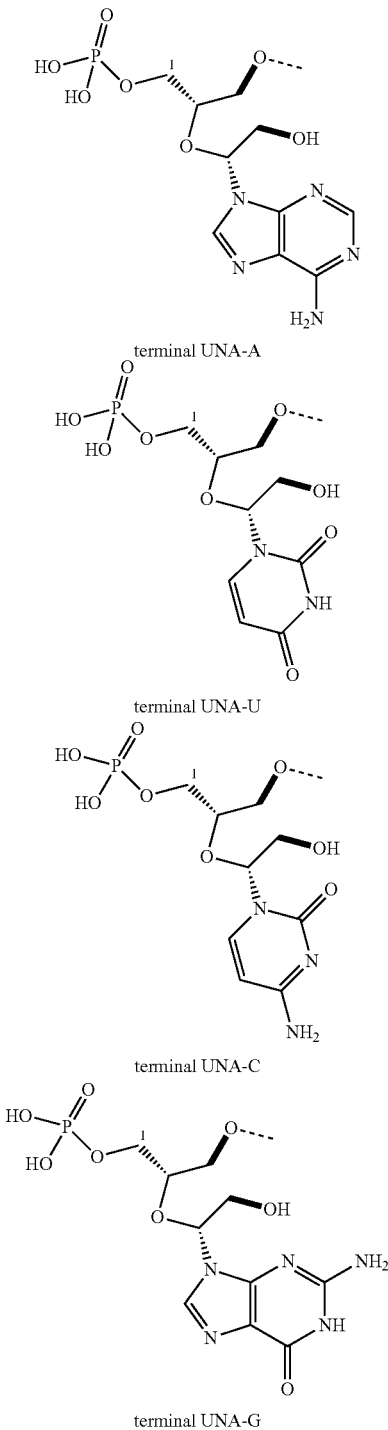

Because a UNA monomer can be a flexible molecule, a UNA monomer as a terminal monomer can assume widely differing conformations. An example of an energy minimized UNA monomer conformation as a terminal monomer attached at the propane-3-yl position is shown below.

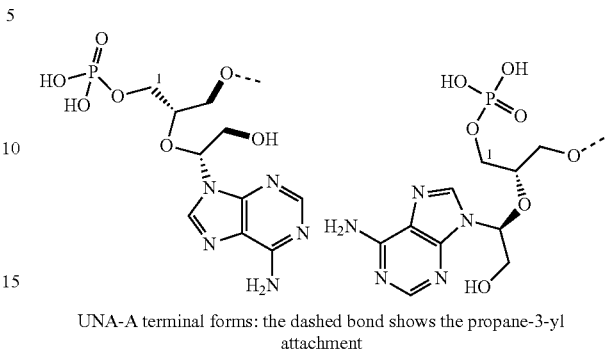

UNA-A terminal forms: the dashed bond shows the propane-3-yl attachment

Thus, UNA oligomers having a terminal UNA monomer are significantly different in structure from conventional nucleic acid agents, such as siRNAs. For example, siRNAs may require that terminal monomers or overhangs in a duplex be stabilized. In contrast, the conformability of a terminal UNA monomer can provide UNA oligomers with different properties.

Among other things, the structure of the UNA monomer allows it to be attached to naturally-occurring nucleotides. A UNA oligomer can be a chain composed of UNA monomers, as well as various nucleotides that may be based on naturally-occurring nucleosides.

In some embodiments, the functional group $R^3$ of a UNA monomer can be —$OR^4$, —$SR^4$, —$NR^4_2$, —$NH(C=O)R^4$, morpholino, morpholin-1-yl, piperazin-1-yl, or 4-alkanoyl-piperazin-1-yl, where $R^4$ is the same or different for each occurrence, and can be H, alkyl, a cholesterol, a lipid molecule, a polyamine, an amino acid, or a polypeptide.

The UNA monomers are organic molecules. UNA monomers are not nucleic acid monomers or nucleotides, nor are they naturally-occurring nucleosides or modified naturally-occurring nucleosides.

A UNA oligomer of this invention is a synthetic chain molecule. A UNA oligomer of this invention is not a nucleic acid, nor an oligonucleotide.

In some embodiments, as shown above, a UNA monomer can be UNA-A (designated A), UNA-U (designated U), UNA-C (designated C), and UNA-G (designated C).

Designations that may be used herein include mA, mG, mC, and mU, which refer to the 2'-O-Methyl modified ribonucleotides.

Designations that may be used herein include lower case c and u, which refer to the 2'-O-methyl modified ribonucleotides.

Designations that may be used herein include dT, which refers to a 2'-deoxy T nucleotide.

Monomers for UNA oligomers

As used herein, in the context of oligomer sequences, the symbol X represents a UNA monomer.

As used herein, in the context of oligomer sequences, the symbol N represents any natural nucleotide monomer, or a modified nucleotide monomer.

As used herein, in the context of oligomer sequences, the symbol Q represents a non-natural, modified, or chemically-modified nucleotide monomer. When a Q monomer appears in one strand of the oligomer, and is unpaired with the other strand, the monomer can have any base attached. When a Q monomer appears in one strand of the oligomer, and is paired with a monomer in the other strand, the Q monomer can have any base attached that would be complementary to the monomer in the corresponding paired position in the other strand.

Examples of nucleic acid monomers include non-natural, modified, and chemically-modified nucleotides, including any such nucleotides known in the art.

Examples of non-natural, modified, and chemically-modified nucleotide monomers include 2'-O-methyl ribonucleotides, 2'-O-methyl purine nucleotides, 2'-deoxy-2'-fluoro ribonucleotides, 2'-deoxy-2'-fluoro pyrimidine nucleotides, 2'-deoxy ribonucleotides, 2'-deoxy purine nucleotides, universal base nucleotides, 5-C-methyl-nucleotides, and inverted deoxyabasic monomer residues.

Examples of non-natural, modified, and chemically-modified nucleotide monomers include 3'-end stabilized nucleotides, 3'-glyceryl nucleotides, 3'-inverted abasic nucleotides, and 3'-inverted thymidine, and L-thymidine.

Examples of non-natural, modified, and chemically-modified nucleotide monomers include locked nucleic acid nucleotides, 2'-O,4'-C-methylene-(D-ribofuranosyl) nucleotides, 2'-methoxyethoxy (MOE) nucleotides, 2'-methyl-thioethyl, 2'-deoxy-2'-fluoro nucleotides, and 2'-O-methyl nucleotides.

Examples of non-natural, modified, and chemically-modified nucleotide monomers include 2'-amino nucleotides, 2'-O-amino nucleotides, 2'-C-allyl nucleotides, and 2'-O-allyl nucleotides.

Examples of non-natural, modified, and chemically-modified nucleotide monomers include $N^6$-methyladenosine nucleotides.

Examples of non-natural, modified, and chemically-modified nucleotide monomers include nucleotide monomers with modified bases 5-(3-amino)propyluridine, 5-(2-mercapto)ethyluridine, 5-bromouridine; 8-bromoguanosine, or 7-deazaadenosine.

Examples of non-natural, modified, and chemically-modified nucleotide monomers include 2'-O-aminopropyl substituted nucleotides.

Examples of non-natural, modified, and chemically-modified nucleotide monomers include 2'-O-guanidinopropyl substituted nucleotides.

Examples of non-natural, modified, and chemically-modified nucleotide monomers include Pseudouridines.

Examples of non-natural, modified, and chemically-modified nucleotide monomers include replacing the 2'—OH group of a nucleotide with a 2'-R, a 2'-OR, a 2'-halogen, a 2'-SR, or a 2'-amino, or a 2'-azido, where R can be H, alkyl, fluorine-substituted alkyl, alkenyl, or alkynyl.

Examples of non-natural, modified, and chemically-modified nucleotide monomers include replacing the 2'—OH group of a nucleotide with a 2'-R or 2'-OR, where R can be CN, $CF_3$, alkylamino, or aralkyl.

Examples of non-natural, modified, and chemically-modified nucleotide monomers include nucleotides with a modified sugar such as an F-HNA, an HNA, a CeNA, a bicyclic sugar, or an LNA.

Examples of non-natural, modified, and chemically-modified nucleotide monomers include 2'-oxa-3'-aza-4'a-carbanucleoside monomers, 3-hydroxymethyl-5-(1H-1,2,3-triazol)-isoxazolidine monomers, and 5'-triazolyl-2'-oxa-3'-aza-4'a-carbanucleoside monomers.

Some examples of modified nucleotides are given in Saenger, Principles of Nucleic Acid Structure, Springer-Verlag, 1984.

Details of UNA Oligomer Structure

Aspects of this invention can provide structures and compositions for UNA-containing oligomeric compounds. The oligomeric agents may incorporate one or more UNA monomers. Oligomeric molecules of this invention can be used as active agents in formulations for gene regulating or gene silencing therapeutics.

In some embodiments, this invention provides oligomeric compounds having a structure that incorporates novel combinations of UNA monomers with certain natural nucleotides, non-natural nucleotides, modified nucleotides, or chemically-modified nucleotides.

In further aspects, the oligomeric compounds can be pharmacologically active molecules. UNA oligomers of this invention can be used as active pharmaceutical ingredients for regulating gene expression, and in RNA interference methods, as well as antisense, RNA blocking, and microRNA strategies.

A UNA oligomer of this invention can have the structure of Formula I

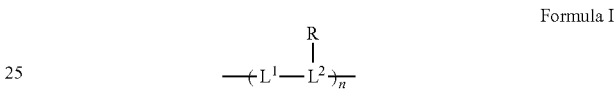

Formula I wherein $L^1$ is a linkage, n is from 19 to 29, and for each occurrence $L^2$ is a UNA linker group having the formula —$C^1$—$C^2$—$C^3$—, where R is attached to $C^2$ and has the formula —$OCH(CH_2R^3)R^5$, where $R^3$ is —$OR^4$, —$SR^4$, —$NR^4_2$, —$NH(C=O)R^4$, morpholino, morpholin-1-yl, piperazin-1-yl, or 4-alkanoyl-piperazin-1-yl, where $R^4$ is the same or different for each occurrence and is H, alkyl, a cholesterol, a lipid molecule, a polyamine, an amino acid, or a polypeptide, and where $R^5$ is a nucleobase, or $L^2(R)$ is a sugar such as a ribose and R is a nucleobase, or $L^2$ is a modified sugar such as a modified ribose and R is a nucleobase. In certain embodiments, a nucleobase can be a modified nucleobase. $L^1$ can be a phosphodiester linkage.

A UNA oligomer of this invention can be a short chain molecule. A UNA oligomer can be a duplex pair. Thus, a UNA oligomer can have a first strand of the duplex and a second strand of the duplex, which is complementary to the first strand with respect to the nucleobases, although up to three mismatches can occur. A UNA oligomer duplex can have overhangs.

Some UNA oligomers are discussed in U.S. Pat. No. 8,314,227, as well as US Patent Publication No. 20110313020 A1.

The target of a UNA oligomer can be a target nucleic acid. In some embodiments, the target can be any TTR mRNA of a subject. A UNA oligomer can be active for gene silencing in RNA interference.

A UNA oligomer may comprise two strands that together provide a duplex. The duplex may be composed of a first strand, which may also be referred to as a passenger strand or sense strand, and a second strand, which may also be referred to as a guide strand or antisense strand.

In some aspects, a UNA oligomer of this invention can have any number of phosphorothioate intermonomer linkages in any position in any strand, or in both strands of a duplex structure.

In certain embodiments, a UNA oligomer of this invention can have a phosphorothioate intermonomer linkage between the last one or two monomers at either end of any strand.

In some embodiments, any one or more of the intermonomer linkages of a UNA oligomer can be a phosphodiester, a phosphorothioate including dithioates, a chiral phosphorothioate, and other chemically modified forms.

Examples of UNA oligomers of this invention include duplex pairs, which are in general complementary. Thus, for example, SEQ ID NO: 1 can represent a first strand of a duplex and SEQ ID NO:2 can represent a second strand of the duplex, which is complementary to the first strand.

For example, the symbol "N" in the first strand can represent any nucleotide that is complementary to the monomer in the corresponding position in the second strand. Example UNA oligomers of this disclosure are shown with 2-monomer length overhangs, although overhangs of from 1 to 8 monomers, or longer, can be used.

The symbol "X" in a strand or oligomer represents a UNA monomer. When a UNA monomer appears in one strand of the oligomer, and is unpaired with the other strand, the monomer can have any base attached. When a UNA monomer appears in one strand of the oligomer, and is paired with a monomer in the other strand, the UNA monomer can have any base attached that would be complementary to the monomer in the corresponding paired position in the other strand.

Further, when the oligomer terminates in a UNA monomer, the terminal position has a 1-end, according to the positional numbering shown above, instead of a 5'-end as for a nucleotide, or the terminal position has a 3-end, according to the positional numbering shown above, instead of a 3'-end as for a nucleotide. For example, the UNA oligomer

```
                                              SEQ ID NO: 1
1-X•N•N•N•N•N•N•N•N•N•N•N•N•N•N•N•N•X•X-3

SEQ ID NO: 2
3-X•X•N•N•N•N•N•N•N•N•N•N•X•X•X•X•X•X•N-5'
``` has a UNA monomer 1-end on the first strand, a UNA monomer 3-end on the first strand, a UNA monomer 3-end on the second strand, and a nucleotide 5'-end on the second strand.

Complementarity of strands can involve mismatches. In certain embodiments, complementarity of strands can include one to three, or more, mismatches.

In some embodiments, a UNA oligomer of this invention can have one or more UNA monomers at the 1-end of the first strand, and one or more UNA monomers at the 3-end of the first strand.

In further embodiments, a UNA oligomer of this invention can have one or more UNA monomers at the 3-end of the second strand.

In certain embodiments, a duplex UNA oligomer of this invention can have one or more UNA monomers at the 1-end of the first strand, one or more UNA monomers at the 3-end of the first strand, and one or more UNA monomers at the 3-end of the second strand.

A UNA oligomer of this invention the oligomer may have a first strand and a second strand, each of the strands independently being 19-23 monomers in length.

In certain embodiments, a UNA oligomer of this invention may have a first strand that is 19-23 monomers in length.

In certain embodiments, a UNA oligomer of this invention may have a duplex region that is 19-21 monomers in length.

In further embodiments, a UNA oligomer of this invention may have a second strand that is 19-23 monomers in length.

In certain embodiments, a UNA oligomer of this invention may have a first strand that is 19 monomers in length, and a second strand that is 21 monomers in length.

In certain embodiments, a UNA oligomer of this invention may have a first strand that is 20 monomers in length, and a second strand that is 21 monomers in length.

In certain embodiments, a UNA oligomer of this invention may have a first strand that is 21 monomers in length, and a second strand that is 21 monomers in length.

In certain embodiments, a UNA oligomer of this invention may have a first strand that is 22 monomers in length, and a second strand that is 21 monomers in length.

A UNA oligomer of this invention for inhibiting gene expression can have a first strand and a second strand, each of the strands being 19-29 monomers in length. The monomers can be UNA monomers and nucleic acid nucleoside monomers. The oligomer can have a duplex structure of from 14 to 29 monomers in length. The UNA oligomer can be targeted to a target gene and can exhibit reduced off-target effects as compared to a conventional siRNA. In some embodiments, a UNA oligomer of this invention can have a first strand and a second strand, each of the strands being 19-23 monomers in length.

In another aspect, the UNA oligomer may have a blunt end, or may have one or more overhangs. In some embodiments, the first and second strands may be connected with a connecting oligomer in between the strands, and form a duplex region with a connecting loop at one end.

In certain embodiments, an overhang can be one or two monomers in length.

Examples of an overhang can contain one or more UNA monomers, natural nucleotides, non-natural nucleotides, modified nucleotides, or chemically-modified nucleotides, and combinations thereof.

Examples of an overhang can contain one or more deoxythymidine nucleotides, 2'-O-methyl nucleotides, inverted abasic monomers, inverted thymidine monomers, L-thymidine monomers, or glyceryl nucleotides.

A UNA oligomer can mediate cleavage of a target nucleic acid in a cell. In some processes, the second strand of the UNA oligomer, at least a portion of which can be complementary to the target nucleic acid, can act as a guide strand that can hybridize to the target nucleic acid.

The second strand can be incorporated into an RNA Induced Silencing Complex (RISC). In some embodiments, a UNA oligomer may have a strand that is a DICER substrate.

A UNA oligomer of this disclosure may comprise naturally-occurring nucleic acid nucleotides, and modifications thereof that are compatible with gene silencing activity.

In some aspects, a UNA oligomer is a double stranded construct molecule that is able to inhibit gene expression.

As used herein, the term strand refers to a single, contiguous chain of monomers, the chain having any number of internal monomers and two end monomers, where each end monomer is attached to one internal monomer on one side, and is not attached to a monomer on the other side, so that it ends the chain.

The monomers of a UNA oligomer may be attached via phosphodiester linkages, phosphorothioate linkages, gapped linkages, and other variations.

In some embodiments, a UNA oligomer can include mismatches in complementarity between the first and second strands. In other embodiments, a UNA oligomer may have 1, or 2, or 3 mismatches. The mismatches may occur at any position in the duplex region.

The target of a UNA oligomer can be a target nucleic acid of a target gene.

A UNA oligomer may have one or two overhangs outside the duplex region. The overhangs can be an unpaired portion at the end of the first strand or second strand. The lengths of the overhang portions of the first and second strands can be the same or different.

A UNA oligomer may have at least one blunt end. A blunt end does not have an overhang portion, and the duplex region at a blunt end terminates at the same position for both the first and second strands.

A UNA oligomer can be RISC length, which means that it has a duplex length of less than 25 base pairs.

In certain embodiments, a UNA oligomer can be a single strand that folds upon itself and hybridizes to itself to form a double stranded region having a connecting loop at the end of the double stranded region.

Examples of UNA oligomer structures of this invention are shown in Table 1.

TABLE 1

Examples of UNA oligomer structures.

| Oligomer | First strand 1 to 3' | Second strand 5' to 3' |
|---|---|---|
| P15U6 | SEQ ID NO: 3<br>ĞGCCAUGCAUGUGUUCAGAÃŨmU | SEQ ID NO: 4<br>UCUGAÃCACAUGCAUGGCCŨmU |
| P15U7 | SEQ ID NO: 5<br>ĞGCCAUGCAUGUGUUCAGAŨmU | SEQ ID NO: 6<br>UCUGAAĈACAUGCAUGGCCŨmU |
| P15U14 | SEQ ID NO: 7<br>ĞGCCAUGCAUGUGUUCAGAŨmU | SEQ ID NO: 8<br>UCUGAACACAUGCÃUGGCCŨmU |
| P15U15 | SEQ ID NO: 9<br>ĞGCCAUGCAUGUGUUCAGAŨmU | SEQ ID NO: 10<br>UCUGAACACAUGCAŨGGCCŨmU |
| P15U16 | SEQ ID NO: 11<br>ĞGCCAUGCAUGUGUUCAGAŨmU | SEQ ID NO: 12<br>UCUGAACACAUGCAUĞGCCŨmU |

Examples of UNA oligomer structures of this invention are shown in Table 2.

TABLE 2

Examples of UNA oligomer structures.

| Oligomer | First strand 1 to 3' | Second strand 5' to 3' |
|---|---|---|
| P16U6 | SEQ ID NO: 13<br>ĞCCAUGCAUGUGUUCAGAAŨmU | SEQ ID NO: 14<br>UUCUGÃACACAUGCAUGGCŨmU |
| P16U7 | SEQ ID NO: 15<br>ĞCCAUGCAUGUGUUCAGAAŨmU | SEQ ID NO: 16<br>UUCUGAÃCACAUGCAUGGCŨmU |
| P16U15 | SEQ ID NO: 17<br>ĞCCAUGCAUGUGUUCAGAAŨmU | SEQ ID NO: 18<br>UUCUGAACACAUGCÃUGGCŨmU |
| P16U16 | SEQ ID NO: 19<br>ĞCCAUGCAUGUGUUCAGAAŨmU | SEQ ID NO: 20<br>UUCUGAACACAUGCAŨGGCŨmU |
| P16U17 | SEQ ID NO: 21<br>ĞCCAUGCAUGUGUUCAGAAŨmU | SEQ ID NO: 22<br>UUCUGAACACAUGCAUĞGCŨmU |

Examples of sequences of UNA oligomers of this invention targeted to a TTR component are shown in Table 3. "Ref Pos" refers to reference position, which is the numerical position of a reference nucleotide in a TTR mRNA. In Table 3, a UNA oligomer would be composed of pairs SEQ ID NOs:23 and 63, 24 and 64, etc.

TABLE 3

UNA oligomers for TTR component target sequences

| REF POS | SEQ ID NO | Sense (5'-3')<br>SEQ ID NOS: 23 to 62 | SEQ ID NO | Antisense (5'-3')<br>SEQ ID NOS: 63 to 102 |
|---|---|---|---|---|
| 626 | 23 | AUGUAACCAAGAGUAUUCCAUUUUUac | 63 | GUAAAAAUGGAAUACUCUUGGUUACAU |
| 626 | 24 | AUGUAACCAAGAGUAUUCCAUUUUUac | 64 | GUAAAAAUGGAAUACUCUUGGUUACAŨ |
| 626 | 25 | ÃUGUAACCAAGAGUAUUCCAUUUUUac | 65 | GUAAAAAUGGAAUACUCUUGGUUACAU |

TABLE 3-continued

UNA oligomers for TTR component target sequences

| REF POS | SEQ ID NO | Sense (5'-3') SEQ ID NOS: 23 to 62 | SEQ ID NO | Antisense (5'-3') SEQ ID NOS: 63 to 102 |
|---|---|---|---|---|
| 626 | 26 | AUGUAACCAAGAGUAUUCCAUUUUUac | 66 | GUAAAAUGGAAUACUCUUGGUUACAŨ |
| 626 | 27 | AUGUAACCAAGAGUAUUCCAUUUUUAĈ | 67 | GUAAAAUGGAAUACUCUUGGUUACAŨ |
| 626 | 28 | AUGUAACCAAGAGUAUUCCAŨUUUac | 68 | GUAAAAUGGAAŨACUCUUGGUUACAŨ |
| 628 | 29 | GUAACCAAGAGUAUUCCAUUUUUACta | 69 | UAGUAAAAUGGAAUACUCUUGGUUAC |
| 628 | 30 | ĜŨAACCAAGAGUAUUCCAUUUUUACta | 70 | UAGUAAAAUGGAAUACUCUUGGUUAC |
| 628 | 31 | GUAACCAAGAGUAUUCCAUUUUUACta | 71 | UAGUAAAAUGGAAUACUCUUGGUUAĈ |
| 628 | 32 | ĜŨAACCAAGAGUAUUCCAUUUUUACta | 72 | UAGUAAAAUGGAAUACUCUUGGUUAĈ |
| 628 | 33 | GUAACCAAGAGUAUUCCAUUUUUACUA | 73 | UAGUAAAAUGGAAUACUCUUGGUUAĈ |
| 628 | 34 | GUAACCAAGAGUAUUCCAUŨŨUUACUA | 74 | UAGUAAAAUGGAAUACUCUUGGUUAĈ |
| 628 | 35 | ĜUAACCAAGAGUAUUCCAUtt | 75 | AUGGAAUACUCUUGGUUACtt |
| 628 | 36 | GUAACCAAGAGUAUUCCAUtt | 76 | AUGGAAUACUCUUGGUUACŨŨ |
| 628 | 37 | ĜUAACCAAGAGUAUUCCAUtt | 77 | AUGGAAUACUCUUGGUUACŨŨ |
| 628 | 38 | GUAACCAAGAGUAUUCCAUŨŨ | 78 | AUGGAAUACUCUUGGUUACŨŨ |
| 628 | 39 | ĜUAACCAAGAGUAUUCCAUŨŨ | 79 | AUGGAAUACUCUUGGUUACŨŨ |
| 628 | 40 | GUAACCAAGAGUAUUCCAUŨŨ | 80 | AUGGAAŨACUCUUGGUUACŨŨ |
| 628 | 41 | ĜUAACCAAGAGUAUUCCAUŨŨ | 81 | AUGGAAŨACUCUUGGUUACŨŨ |
| 628 | 42 | ĜUAACCAAGAGUAUUCCAUŨŨ | 82 | AUGGAAŨACUCUUGGUUACAŨ |
| 628 | 43 | ĜUAACCAAGAGUAUUCCAUŨmU | 83 | AUGGAAUACUCUUGGUUACŨmU |
| 628 | 44 | ĜUAACCAAGAGUAUUCCAUŨmU | 84 | AUGĞAAUACUCUUGGUUACŨmU |
| 628 | 45 | ĜUAACCAAGAGUAUUCCAUŨmU | 85 | AUGGAAUACUCUUGGUUACŨmU |
| 628 | 46 | ĜUAACCAAGAGUAUUCCAUŨmU | 86 | AUGGAAUACUCUUGGUUACŨmU |
| 626 | 47 | AUGUAACCAAGAGUAUUCCŨmU | 87 | GGAAUACUCUUGGUUACAUŨmU |
| 626 | 48 | AUGUAACCAAGAGUAUUCCŨmU | 88 | GGAAUACUCUUGGUUACAUŨmU |
| 626 | 49 | AUGUAACCAAGAGUAUUCCŨmU | 89 | GGAAŨACUCUUGGUUACAUŨmU |
| 626 | 50 | AUGUAACCAAGAGUAUUCŨmU | 90 | GGAAUACUCUUGGUUACAUŨmU |
| 635 | 51 | AGAGUAUUCCAUUUUUACŨmU | 91 | AGUAAAAUGGAAUACUCŨmU |
| 635 | 52 | AGAGUAUUCCAUUUUUACŨmU | 92 | AGUAAAAUGGAAUACUCUmU |
| 635 | 53 | AGAGUAUUCCAUUUUUACŨmU | 93 | AGUAAAAUGGAAUACUCŨmU |
| 635 | 54 | AGAGUAUUCCAUUUUUACŨmU | 94 | AGUAAAAUGGAAUACUCŨmU |
| 174 | 55 | ĜACUGGUAUUUGUGUCUGAŨmU | 95 | UCAGACACAAAUACCAGUCĈmA |
| 174 | 56 | ĜACUGGUAUUUGUGUCUGAŨmU | 96 | UCAĞACACAAAUACCAGUCĈmA |
| 174 | 57 | ĜACUGGUAUUUGUGUCUGAŨmU | 97 | UCAGACACAAAUACCAGUCĈmA |
| 174 | 58 | ĜACUGGUAUUUGUGUCUGAŨmU | 98 | UCAGAĈACAAAUACCAGUCĈmA |
| 627 | 59 | ŨGUAACCAAGAGUAUUCCAŨmU | 99 | UGGAAUACUCUUGGUUACAŨmU |
| 629 | 60 | ŨAACCAAGAGUAUUCCAUUŨmU | 100 | AAUGGAAUACUCUUGGUUAŨmU |
| 632 | 61 | ĈCAAGAGUAUUCCAUUUUŨmU | 101 | AAAAUGGAAUACUCUUGGŨmU |
| 632 | 62 | ĈCAAGAGUAUUCCAUUUUUŨmU | 102 | AAAAUĞGAAUACUCUUGGŨmU |

In Table 3, lower case designates 2'-deoxyribo-N; upper case designates Ribo-N; underlined-lower case designates 2'-deoxy-N; mA, mG, mC, and mU designate 2'-O-Methyl RNA; and A U G and C designate UNA monomers.

In certain embodiments, a UNA oligomer may have a duplex region, and have a UNA monomer in the second strand within the duplex region, where the UNA monomer in the second strand is present in any of positions 1 through 19, counting from the 5' end of the second strand.

In certain embodiments, a UNA oligomer may have a duplex region, and have a UNA monomer in the second strand within the duplex region, where the UNA monomer in the second strand is present in any of positions 6, 7, 14, 15 and 16, counting from the 5' end of the second strand.

In some embodiments, a UNA oligomer may comprise an overhang portion of two monomers in length, or longer, at the 3' end of the first strand, wherein the overhang monomer immediately flanking the duplex portion is a UNA monomer.

In some embodiments, a UNA oligomer may comprise an overhang portion of two monomers in length, or longer, at the 3' end of the second strand, wherein the overhang monomer immediately flanking the duplex portion is a UNA monomer.

Methods for Treating Amyloidosis

Methods of this invention include the treatment and prevention of TTR-related amyloidosis in human and mammalian subjects.

In the methods of this invention, a subject in need of treatment or prevention can be administered an effective amount of a UNA oligomer. Administration can be performed for 1, 2, or up to 7 days, or 1, 2, 3, or up to 4 weeks, or longer.

The subject may have TTR-related amyloidosis, also known as ATTR.

In particular, a subject can have a V30M gene. The methods of this invention can selectively reduce V30M TTR in the subject.

In some embodiments, a method of this invention can selectively reduce V30M TTR in the subject by at least 10%, as compared to control. In certain embodiments, V30M TTR in the subject can be reduced by at least 20%, or 30%, or 50%, as compared to control.

An effective amount of a UNA oligomer of this invention can be a dose ranging from 0.001 mg/kg to 50.0 mg/kg, or from 0.001 mg/kg to 10.0 mg/kg.

In the methods of this invention, TTR mRNA expression can be reduced in a subject for at least 5 days. In certain embodiments, TTR mRNA expression can be reduced in a subject for at least 10 days, or 15 days.

In the methods of this invention, peripheral neuropathy or autonomic neuropathy in the subject can be reduced.

In the methods of this invention, peripheral neuropathy or autonomic neuropathy in the subject can be reduced. In some embodiments, a subject may undergo reduced lower extremity weakness, reduced pain, or improved sensation. Methods of this invention can reduce occurrence of vitreous opacities in the subject.

In the methods of this disclosure, the administration of a UNA oligomer may not result in an inflammatory response.

In further embodiments, this invention includes methods for inhibiting expression of a TTR gene in a cell, by treating the cell with a UNA oligomer.

In additional embodiments, this invention includes methods for inhibiting expression of a TTR gene in a mammal, by administering to the mammal a composition containing a UNA oligomer.

Pharmaceutical Compositions

In some aspects, this invention provides compositions containing a UNA oligomer and a pharmaceutically acceptable carrier.

In further aspects, this invention includes nanoparticle compositions that can encapsulate and deliver a UNA oligomer to cells with surprisingly advantageous potency. The nanoparticles can be formed with lipid molecules, for example, any one or more of the compounds ATX-001 to ATX-032 disclosed in WO/2015/074085 and provided below in Table 4. In certain embodiments, lipid nanoparticles of this invention can be formed with compound ATX-002, as disclosed in WO/2015/074085, and the nanoparticles can encapsulate the UNA oligomer.

TABLE 4

Compounds ATX-001 to ATX-032

| Lipid ID | Novel Lipid | MW | pKa | KD @ 0.3 mg/kg |
|---|---|---|---|---|
| ATX-001 | 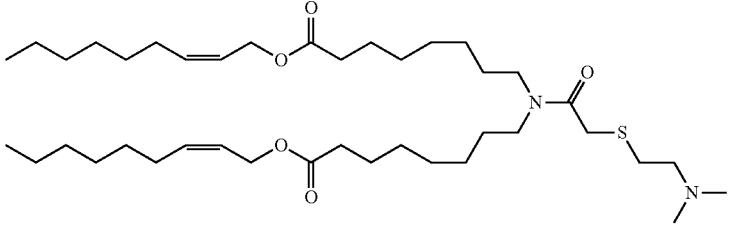 | 695.1 | 8.9 | ~0 |
| ATX-002 | 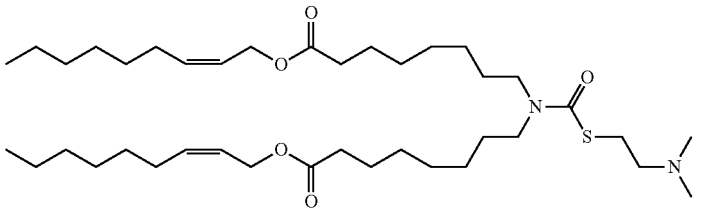 | 681 | 8.7 | 98 |

TABLE 4-continued

Compounds ATX-001 to ATX-032

| Lipid ID | Novel Lipid | MW | pKa | KD @ 0.3 mg/kg |
|---|---|---|---|---|
| ATX-003 | | 695.1 | 9.3 | ~0 |
| ATX-004 | | 709.13 | 9.4 | ~0 |
| ATX-005 | | 709.13 | 9.0 | ~0 |
| ATX-006 | | 723.15 | 9.8 | ~0 |
| ATX-007 | | 723.14 | 9.5 | n/a |
| ATX-008 | | 737.18 | 10 | n/a |

TABLE 4-continued

Compounds ATX-001 to ATX-032

| Lipid ID | Novel Lipid | MW | pKa | KD @ 0.3 mg/kg |
|---|---|---|---|---|
| ATX-009 | | 695.1 | 8.8 | ~0 |
| ATX-010 | | 709.13 | 9.6 | 30 |
| ATX-011 | | 709.13 | 9.4 | n/a |
| ATX-012 | | 723.15 | 10 | ~0 |
| ATX-013 | | 681.01 | | n/a |
| ATX-014 | | 695.1 | | n/a |

TABLE 4-continued

Compounds ATX-001 to ATX-032

| Lipid ID | Novel Lipid | MW | pKa | KD @ 0.3 mg/kg |
|---|---|---|---|---|
| ATX-015 | | 695.1 | | n/a |
| ATX-016 | | 709.13 | | 15 |
| ATX-017 | | 695.1 | | n/a |
| ATX-018 | | 554.92 | | 40 (@.50 mpk) |
| ATX-019 | | 611.03 | | 30 (@.50 mpk) |
| ATX-020 | | 667.13 | | 40 (@.05 mpk) |

TABLE 4-continued
Compounds ATX-001 to ATX-032
| Lipid ID | Novel Lipid | MW | pKa | KD @ 0.3 mg/kg |
|---|---|---|---|---|
| ATX-021 | 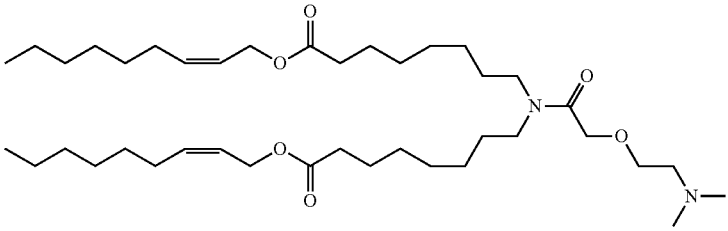 [SMILES: CCCCCC/C=C\COC(=O)CCCCCCCN(CCCCCCCC(=O)OC/C=C\CCCCCC)C(=O)CSCCN(C)C] | 679.04 | | n/a |
| ATX-022 | 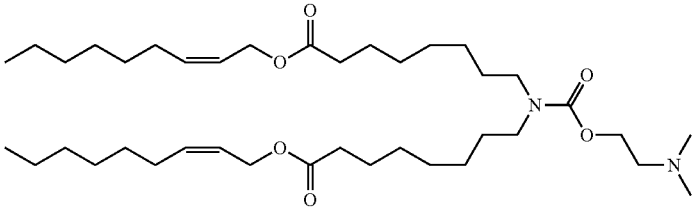 [SMILES: CCCCCC/C=C\COC(=O)CCCCCCCN(CCCCCCCC(=O)OC/C=C\CCCCCC)C(=O)OCCN(C)C] | 665.01 | | n/a |
| ATX-023 | 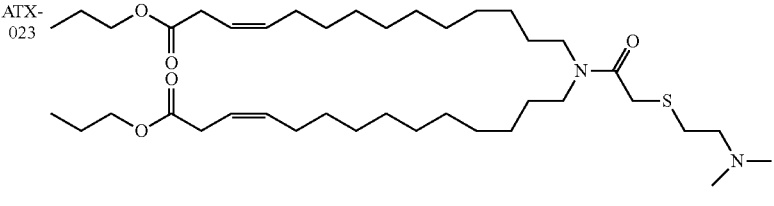 | 695.1 | | n/a |
| ATX-024 | 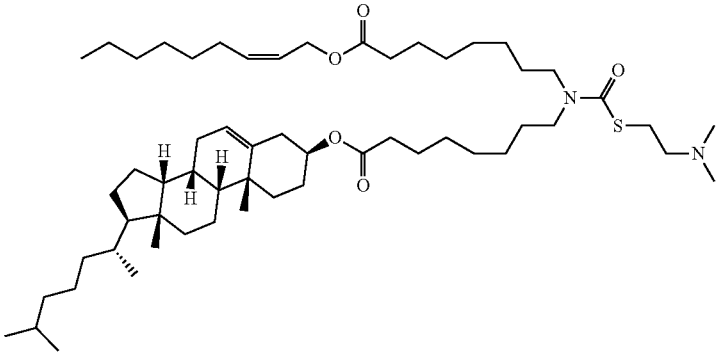 | 925.5 | | 0 |
| ATX-025 | 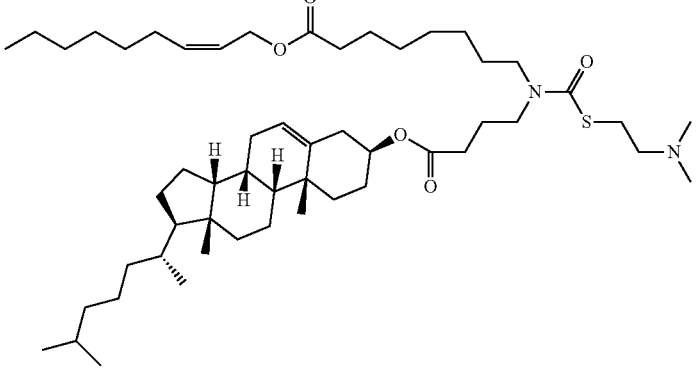 | 869.39 | | 15 |

TABLE 4-continued
Compounds ATX-001 to ATX-032
| Lipid ID | Novel Lipid | MW | pKa | KD @ 0.3 mg/kg |
|---|---|---|---|---|
| ATX-026 | 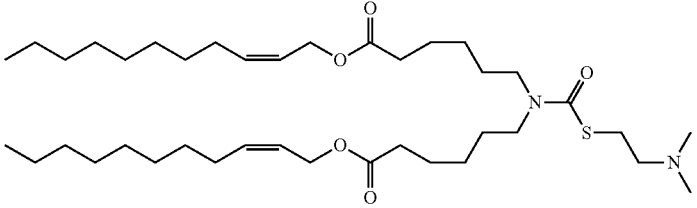 [SMILES: CCCCCCCC/C=C\COC(=O)CCCCCN(CCCCCC(=O)OC/C=C\CCCCCCCC)C(=O)SCCN(C)C] | 681.07 | | n/a |
| ATX-027 | 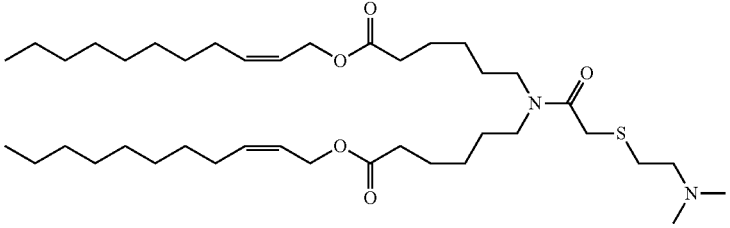 [SMILES: CCCCCCCC/C=C\COC(=O)CCCCCN(CCCCCC(=O)OC/C=C\CCCCCCCC)C(=O)CSCCN(C)C] | 695.1 | | n/a |
| ATX-028 | 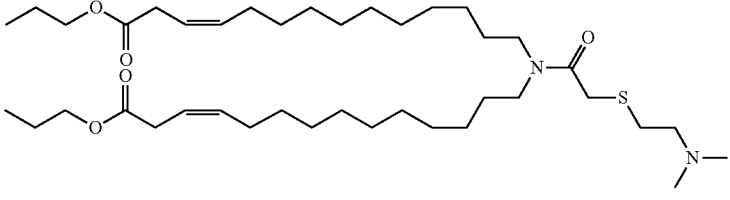 [SMILES: CCCOC(=O)C/C=C\CCCCCCCCCCN(CCCCCCCCCC/C=C\CC(=O)OCCC)C(=O)CSCCN(C)C] | 681.07 | | n/a |
| ATX-029 | 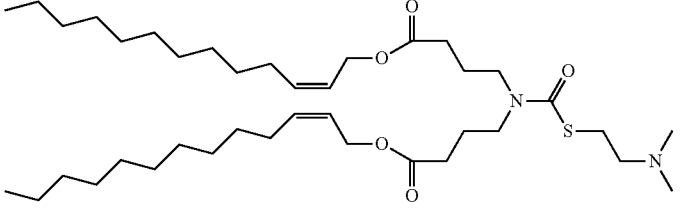 [SMILES: CCCCCCCCCC/C=C\COC(=O)CCCN(CCCC(=O)OC/C=C\CCCCCCCCCC)C(=O)SCCN(C)C] | 681.1 | | n/a |
| ATX-030 | 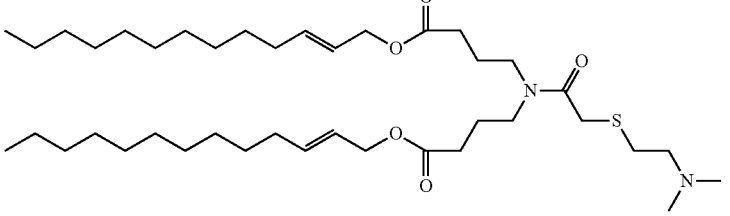 | 695.1 | | n/a |
| ATX-031 | 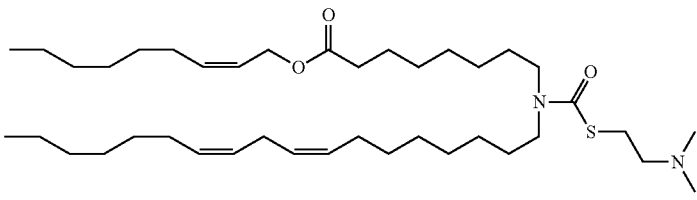 [SMILES: CCCCCC/C=C\C/C=C\CCCCCCCN(CCCCCCCC(=O)OC/C=C\CCCCCC)C(=O)SCCN(C)C] | 663.1 | | n/a |
| ATX-032 | 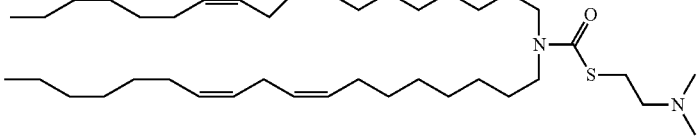 | 645.13 | | n/a |

A composition can be capable of local or systemic administration. In some aspects, a pharmaceutical composition can be capable of any modality of administration. In certain aspects, the administration can be intravenous, subcutaneous, pulmonary, intramuscular, intraperitoneal, dermal, oral, or nasal administration.

Embodiments of this invention include pharmaceutical compositions containing a UNA oligomer in a lipid formulation.

In some embodiments, a composition may comprise one or more lipids selected from cationic lipids, anionic lipids, sterols, pegylated lipids, and any combination of the foregoing.

In certain embodiments, a composition can be substantially free of liposomes.

In further embodiments, a composition can include liposomes.

In additional embodiments, a composition can contain a UNA oligomer within a viral or bacterial vector.

A pharmaceutical composition of this disclosure may include carriers, diluents or excipients as are known in the art. Examples of pharmaceutical compositions are described, for example, in Remington's Pharmaceutical Sciences, Mack Publishing Co. (A. R. Gennaro ed. 1985).

Examples of excipients for a pharmaceutical composition include antioxidants, suspending agents, dispersing agents, preservatives, buffering agents, tonicity agents, and surfactants.

EXAMPLES

Example 1

FIG. 1 shows the single nucleotide polymorph (SNP) that exists at position 284 in the V30M mutation of the human TTR mRNA, as compared to the wild type (WT) TTR mRNA. Conventional siRNAs that are complementary to the WT mRNA were tiled around position 284. FIG. 2 shows that the conventional siRNAs complementary to the WT mRNA have limited activity in silencing the WT TTR gene, as measured by TTR knockdown in HepG2 cells. Positions 5, 9, 14 and 15 appear to be more accessible to silencing than other positions. FIG. 3 shows conventional siRNAs that were complementary to the V30M mRNA were tiled around position 284. Four conventional siRNA variations, namely V30M-P5, V30M-P9, V30M-P14, and V30M-P15, were prepared. Also, as shown in FIG. 3, two gene reporter variants, V30V and V30M, each bearing nucleotide sequence 264 to 304 of human TTR, V30V being without the point mutation at position 284, and V30M containing the point mutation at position 284, were prepared and used in the PSICHECK reporter system in the 3'-UTR region of Luciferase gene.

Example 2

Figure 4:
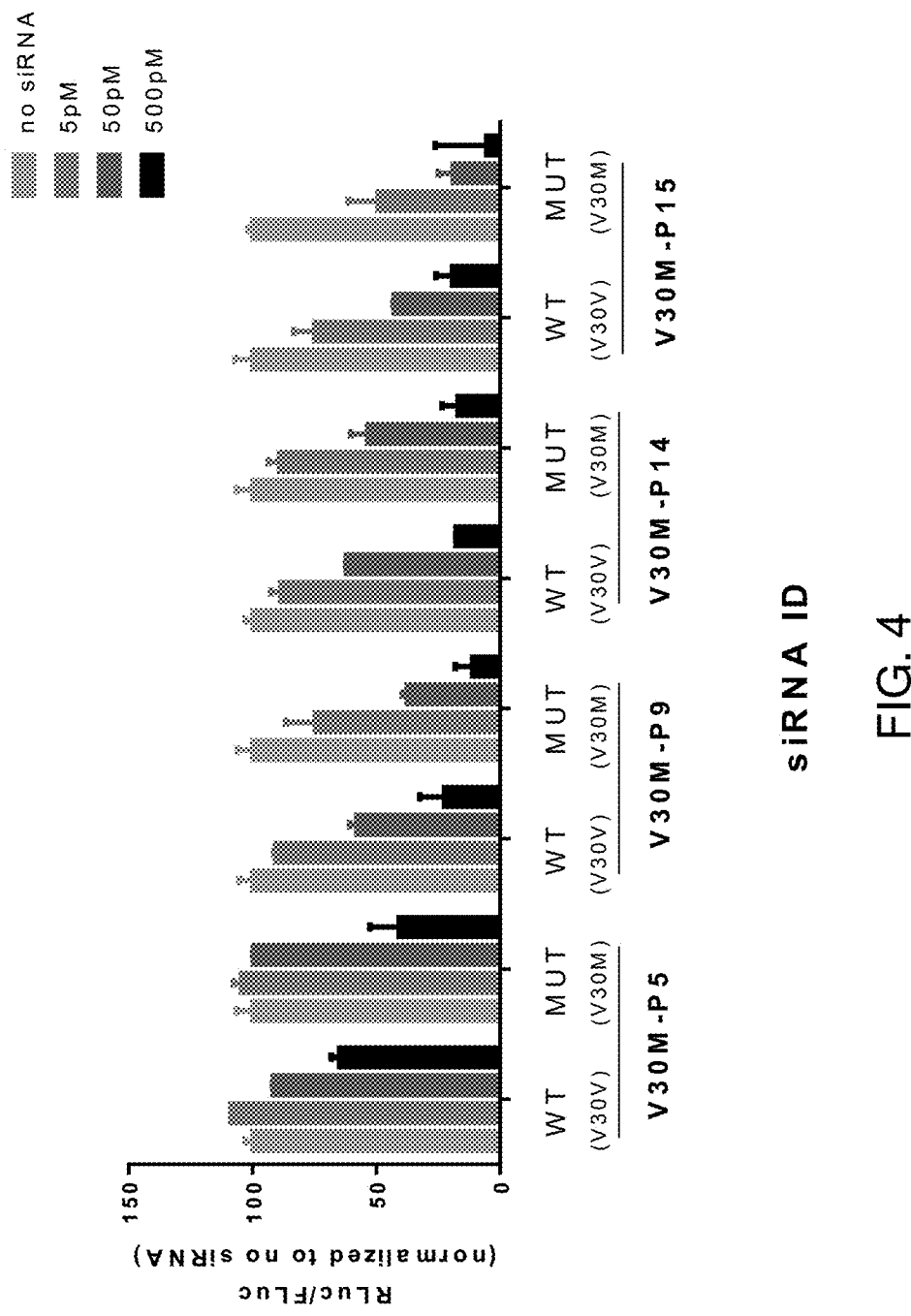
FIG. 4 shows the activity of the four conventional siRNA variations V30M-P5, V30M-P9, V30M-P14, and V30M-P15 measured in the PSICHECK reporter assay against V30V and V30M gene reporter variants. The conventional siRNA variations V30M-P5, V30M-P9, and V30M-P15 were more effective against V30M than V30V. The conventional siRNA variation V30M-P14 was not more effective against V30M than V30V.
Figure 5:
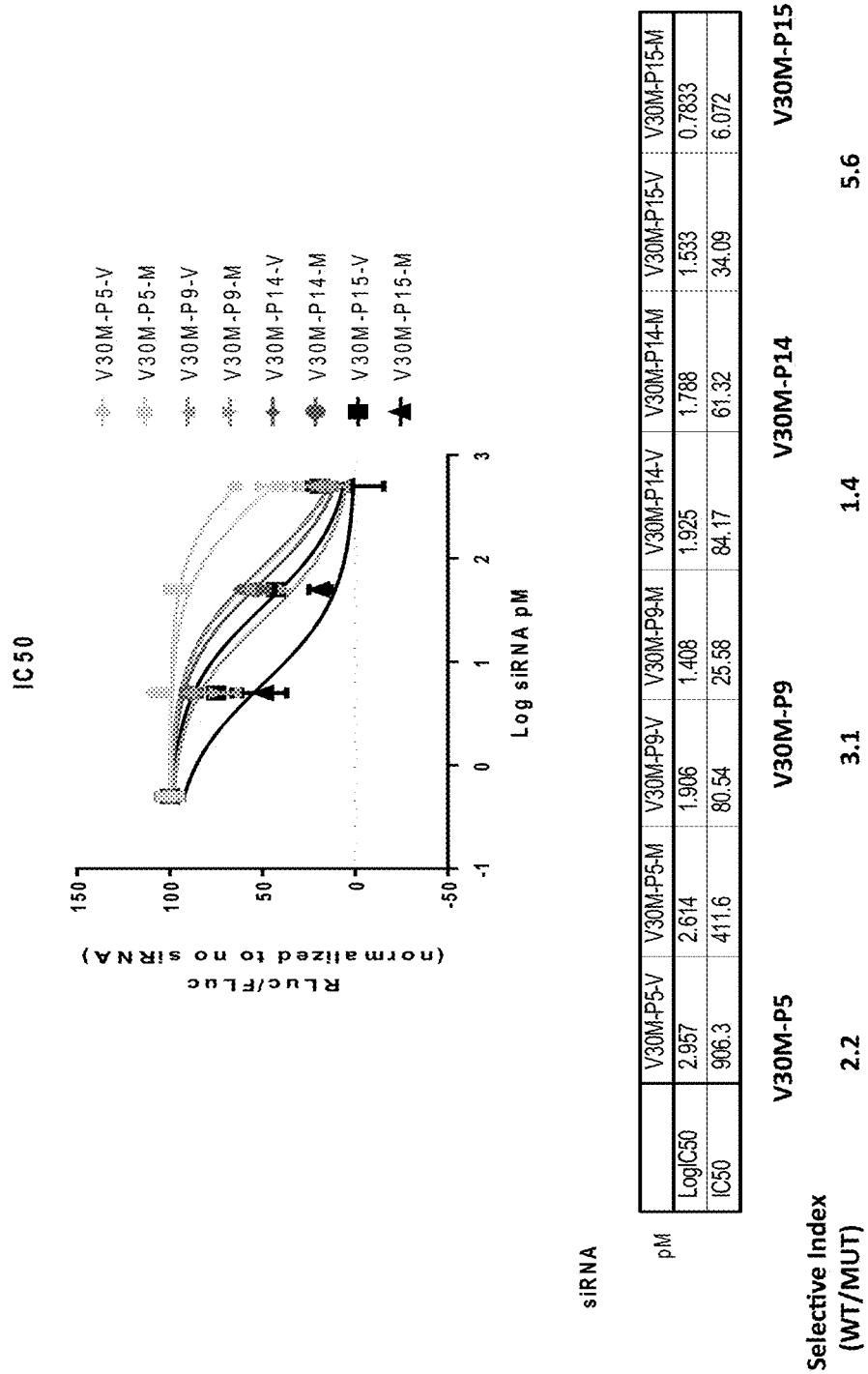
FIG. 5 shows IC50 analysis for the four conventional siRNA variations V30M-P5, V30M-P9, V30M-P14, and V30M-P15 measured in the PSICHECK reporter assay against V30V and V30M gene reporter variants. The conventional V30M-P15 variant was 5.6 times more effective against V30M than V30V. Thus, the selectivity of the conventional siRNAs against V30M over V30V was no more than 5.6.

FIG. 4 shows the activity of the four conventional siRNA variations V30M-P5, V30M-P9, V30M-P14, and V30M-P15 as measured in the PSICHECK reporter assay against V30V and V30M gene reporter variants. The conventional siRNA variations V30M-P5, V30M-P9, and V30M-P15 were more effective against V30M than V30V. The conventional siRNA variation V30M-P14 was not more effective against V30M than V30V. FIG. 5 shows IC50 analysis for the four conventional siRNA variations V30M-P5, V30M-P9, V30M-P14, and V30M-P15 measured in the PSICHECK reporter assay against V30V and V30M gene reporter variants. The conventional V30M-P15 variant was 5.6 times more effective against V30M than V30V. Thus, the selectivity of the conventional siRNAs against V30M over V30V was no more than 5.6.

Example 3

FIG. 6 shows the structure of UNA oligomers that were effective in silencing V30M TTR, as measured in the PSICHECK reporter assay. Each of the UNA oligomer embodiments, P15U6, P15U7, P15U14, P15U15, and P15U16, contained four UNA monomers. In each UNA oligomer, a first UNA monomer was located at the 5' end of the first strand, also called the passenger strand. In each UNA oligomer, the second strand, also called the guide strand, formed a duplex region of 19 monomers length with the first strand. Each UNA oligomer had a duplex region of 19 monomers, and a two-monomer overhang at each end. In each UNA oligomer, a second UNA monomer was located at the 3' end of the first strand, in the $20^{th}$ position, which is in an overhang portion. In each UNA oligomer, a third UNA monomer was located at the 3' end of the second strand, in the $20^{th}$ position, which is in an overhang portion. In the UNA oligomer embodiments, P15U6, P15U7, P15U14, P15U15, and P15U16, a fourth UNA monomer was located in the second strand at positions 6, 7, 14, 15 and 16, respectively, counting from the 5' end of the second strand.

Example 4

Figure 7:
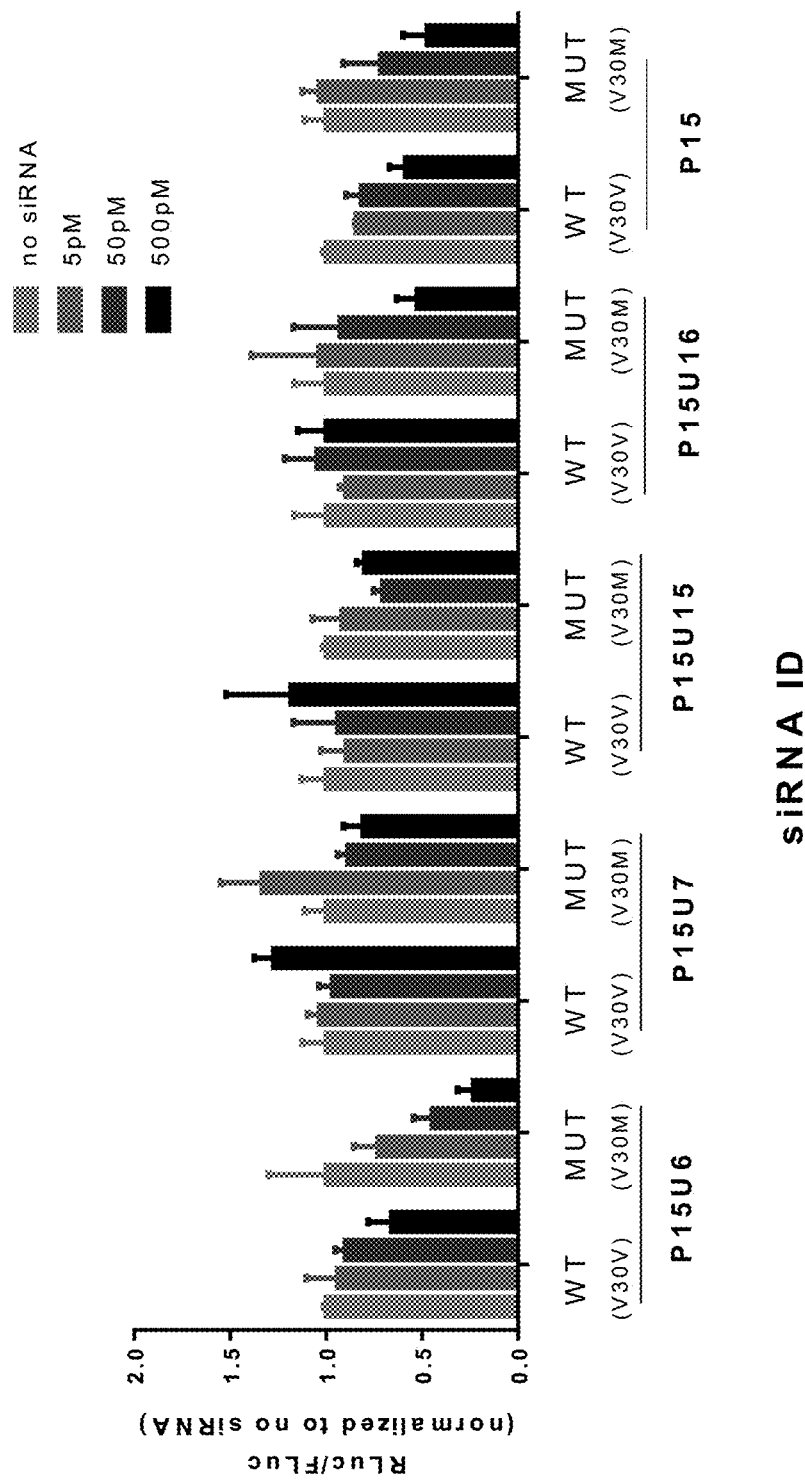
FIG. 7 shows the activity of UNA oligomers P15U6, P15U7, P15U15, and P15U16, measured in the PSICHECK reporter assay against V30V and V30M gene reporter variants, as compared to the conventional siRNA V30M-P15. For each of the UNA oligomer embodiments, P15U6, P15U7, P15U15, and P15U16, the UNA oligomers were more effective against V30M than V30V. Surprisingly, the activity of the UNA oligomer P15U6 was substantially and advantageously superior to the activity of the conventional siRNA V30M-P15, where each is targeted to V30M. Furthermore.

FIG. 7 shows the activity of UNA oligomers P15U6, P15U7, P15U15, and P15U16, measured in the PSICHECK reporter assay against V30V and V30M gene reporter variants, as compared to the conventional siRNA V30M-P15. For each of the UNA oligomer embodiments, P15U6, P15U7, P15U15, and P15U16, the UNA oligomers were more effective against V30M than V30V. Surprisingly, the activity of the UNA oligomer P15U6 was substantially and advantageously superior to the activity of the conventional siRNA V30M-P15, where each is targeted to V30M. Furthermore, FIG. 7 shows the surprising and unexpected result that the selectivity of the UNA oligomers, P15U6, P15U7, P15U15, and P15U16, against V30M over V30V was substantially greater than for the conventional siRNA V30M-P15. In particular, the selectivity of UNA oligomer P15U6 against V30M over V30V was 24, meaning that the IC50 of UNA oligomer P15U6 against V30M (37.6 pM) was 24 times lower than the IC50 of UNA oligomer P15U6 against V30V (919.9 pM). This selectivity was advantageously 4-fold superior to the selectivity of 5.6 shown by the conventional siRNA.

Example 5

FIG. 8 shows the structure of UNA oligomers that were effective in silencing V30M TTR, as measured in the PSICHECK reporter assay. Each of the UNA oligomer embodiments, P16U6, P16U7, P16U15, P16U16, and P16U17, contained four UNA monomers. In each UNA oligomer, a first UNA monomer was located at the 5' end of the first strand, also called the passenger strand. In each UNA oligomer, the second strand, also called the guide strand, formed a duplex region of 19 monomers length with the first strand. Each UNA oligomer had a duplex region of 19 monomers, and a two-monomer overhang at each end. In each UNA oligomer, a second UNA monomer was located at the 3' end of the first strand, in the $20^{th}$ position, which is in an overhang portion. In each UNA oligomer, a third UNA monomer was located at the 3' end of the second strand, in the 20$^{th}$ position, which is in an overhang portion. In the UNA oligomer embodiments, P16U6, P16U7, P16U15, P16U16, and P16U17, a fourth UNA monomer was located in the second strand at positions 6, 7, 15, 16 and 17, respectively, counting from the 5' end of the second strand.

Example 6

Figure 9:
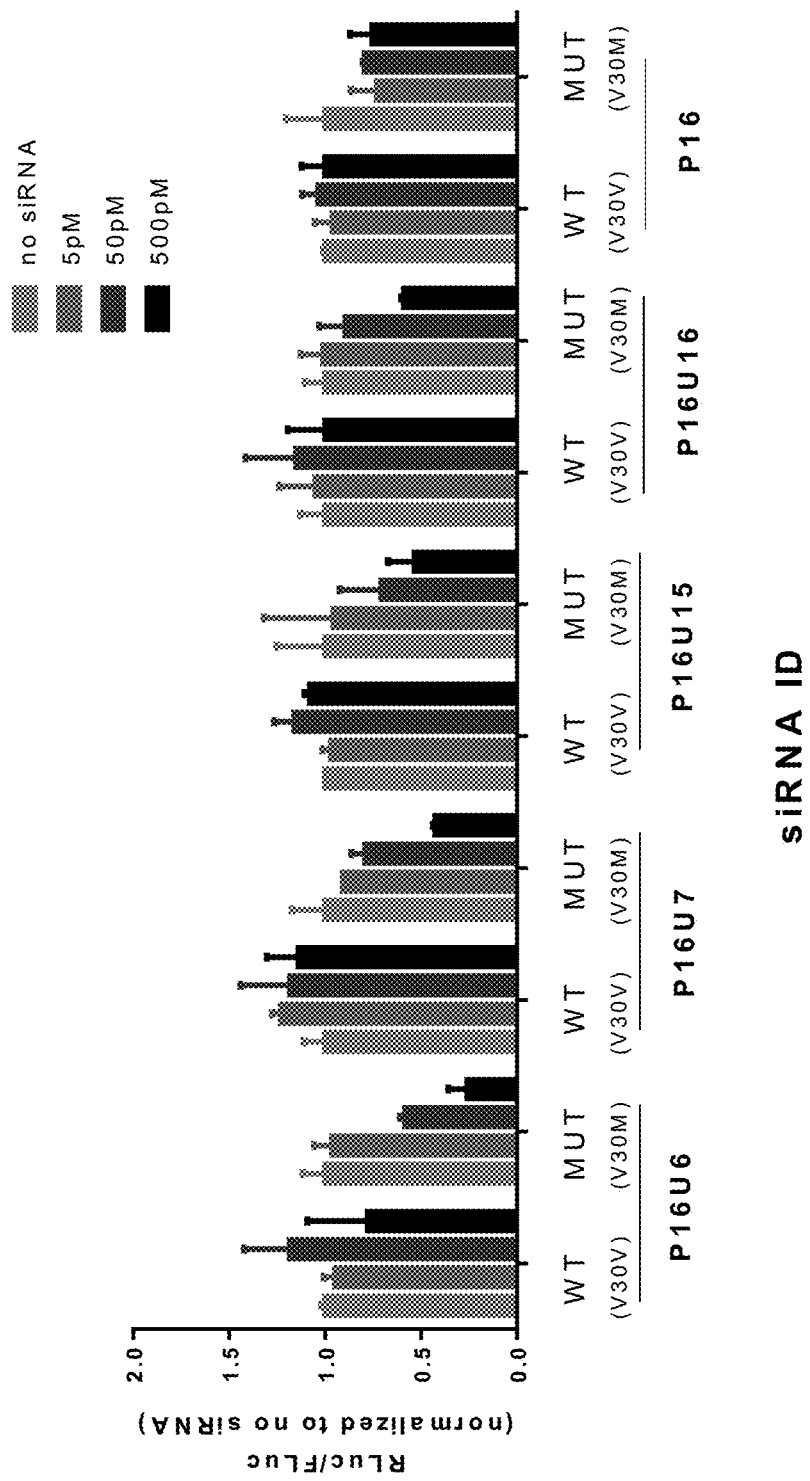
FIG. 9 shows the activity of UNA oligomers P16U6, P16U7, P16U15, and P16U16, measured in the PSICHECK reporter assay against V30V and V30M gene reporter variants, as compared to the conventional siRNA V30M-P16. For each of the UNA oligomer embodiments, P16U6, P16U7, P16U15, and P16U16, the UNA oligomers were more effective against V30M than V30V. Surprisingly, the activity of each of the UNA oligomers P16U6, P16U7, P16U15, and P16U16, was substantially and advantageously superior to the activity of the conventional siRNA V30M-P16, where each is targeted to V30M. Furthermore.

FIG. 9 shows the activity of UNA oligomers P16U6, P16U7, P16U15, and P16U16, measured in the PSICHECK reporter assay against V30V and V30M gene reporter variants, as compared to the conventional siRNA V30M-P16. For each of the UNA oligomer embodiments, P16U6, P16U7, P16U15, and P16U16, the UNA oligomers were more effective against V30M than V30V. Surprisingly, the activity of each of the UNA oligomers P16U6, P16U7, P16U15, and P16U16, was substantially and advantageously superior to the activity of the conventional siRNA V30M-P16, where each is targeted to V30M. Furthermore, FIG. 9 shows the surprising and unexpected result that the selectivity of the UNA oligomers, P16U6, P16U7, P16U15, and P16U16, against V30M over V30V was substantially greater than for the conventional siRNA V30M-P16. In particular, the selectivity of UNA oligomer P16U6 against V30M over V30V was 23, meaning that the IC50 of UNA oligomer P16U6 against V30M (92.4 pM) was 23 times lower than the IC50 of UNA oligomer P16U6 against V30V (2119 pM). This selectivity was advantageously 4-fold superior to the selectivity of 5.6 shown by the conventional siRNA.

Figure 10:
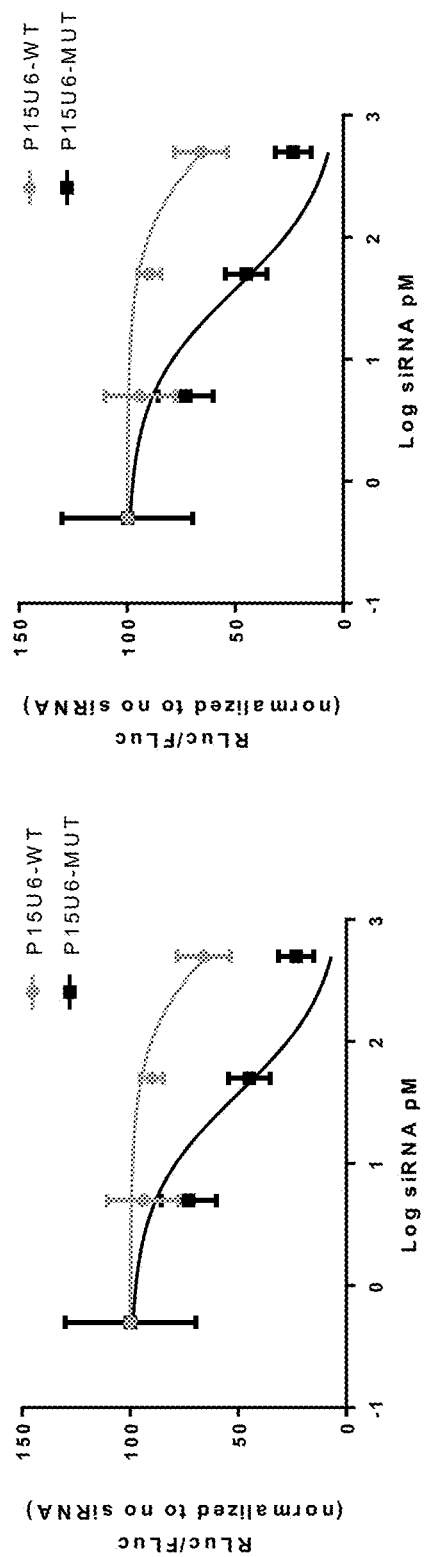
FIG. 10 (left) shows the selectivity of UNA oligomer P15U6 against V30M over V30V. The IC50 of UNA oligomer P15U6 against V30M (37.6 pM) was 24 times lower than the IC50 of UNA oligomer P15U6 against V30V (919.9 pM). This selectivity was advantageously 4-fold superior to the selectivity of 5.6 shown in FIG. 5 above for the conventional siRNA.

FIG. 10 (left) shows the selectivity of UNA oligomer P15U6 against V30M over V30V. The IC50 of UNA oligomer P15U6 against V30M (37.6 pM) was 24 times lower than the IC50 of UNA oligomer P15U6 against V30V (919.9 pM). This selectivity was advantageously 4-fold superior to the selectivity of 5.6 shown by the conventional siRNA. FIG. 10 (right) shows the surprising and unexpected result that the IC50 of UNA oligomer P16U6 against V30M (92.4 pM) was 23 times lower than the IC50 of UNA oligomer P16U6 against V30V (2119 pM). This selectivity was advantageously 4-fold superior to the selectivity of 5.6 shown by the conventional siRNA.

Example 7: UNA Oligomers Reduce V30M TTR Deposits In Vivo

Transgenic mice for human TTR V30M overexpression are used at 6 months age. TTR wild-type and TTR knockout mice are used as controls. Animals are housed in controlled environment, and euthanized with ketamine and medetomidine.

For TTR gene silencing, the TTR UNA oligomer, as well as controls, are delivered in liposome formulations. Mice are injected in the tail vein with TTR UNA oligomer (n=6), at a concentration of 1 mg/kg. Untreated age-matched controls are treated with blank formulation. One injection is given per week for 4 weeks, and animals are sacrificed 48 h after last injection. Liver and colon are removed and collected to 10% formalin and frozen.

Liver and colon mRNA are isolated using phenol extraction (Invitrogen). Sciatic nerve from V30M mice is dissected from other tissue, and mRNA is extracted with a RNeasy Mini column (Qiagen). cDNA is synthesized with a SuperScript double-stranded cDNA Kit (Invitrogen). Extracted RNA is validated with Experion RNA StdSens Analysis Kit (Bio-Rad). qPCR is performed with primers and iQ Syber Green Super Mix (Bio-Rad). Double immunofluorescence analysis is performed with sciatic nerve, dorsal root ganglia, and colon from V30M animals that is removed and treated as above. Comparisons are performed with Student T-test or One-way ANOVA. Data are expressed as mean values±standard error (SEM). p-values less than 0.05 are considered significant.

Injection of a composition containing one or more UNA oligomers in V30M mice reduces the V30M TTR deposits in sciatic nerve, dorsal root ganglia, and colon by at least 90% over controls.

Injection of a composition containing any one of UNA oligomers P15U6, P15U7, P15U15, or P15U16, or any combination of these UNA oligomers, in V30M mice reduces the V30M TTR deposits in sciatic nerve, dorsal root ganglia, and colon by at least 90% over controls.

Example 8: UNA Oligomers Reduce TTR Protein In Vivo Primate

A single-dose, pharmacokinetic and pharmacodynamic study of liposomally formulated UNA Oligomers targeting transthyretin (TTR) mRNA following intravenous infusion in Cynomolgus monkeys was performed.

Cynomolgus monkeys (*Macaca fascicularis*) were selected for this study because the TTR mRNA of Cynomolgus monkeys is homologous to human TTR mRNA, making them a good model for screening the potency of UNA oligomers targeting to TTR mRNA.

In this study, the knockdown of Transthyretin protein was evaluated as a result of treatment with UNA oligomers targeting Transthyretin TTR mRNA, based on SEQ ID NOs:46/86, 59/99, and 60/100, delivered in a liposomal formulation to male Cynomolgus monkeys. Measurements were made following a single intravenous (IV) dose administration. TTR protein concentration in plasma samples was assessed by LC-MS/MS at various time points.

Twenty-four (24) Cynomolgus non-naïve and naïve monkeys were used in this study. There were eight (8) groups of animals in the study with three (3) per group and three (3) extra animals. The animals weighed 2.4 to 6.8 kg and were 3 to 6 years old at pre-study physical examination. Animals were housed in a temperature- and humidity-monitored environment. The targeted range of temperature and relative humidity was from 18° C. to 29° C., and from 35% to 70%, respectively. An automatic lighting system provided a 12-hour light/dark cycle. Previously quarantined animals were acclimated to the study room for a minimum of 14 days prior to initiation of dosing. Acclimation phase data was collected from all animals.

Animals in Groups 1 through 8 were administered the test articles on Day 1 at 0.3 mg/kg, dose volume 6.25 mL/kg, concentration 0.048 mg/mL. Doses were administered as a 15-minute intravenous (IV) infusion, +1 minute, using a pump and disposable syringe.

For each animal, infusion start and end times were recorded; and subsequent sample collection target times were determined based on infusion end time (t=0). All blood specimens, approximately 1 mL, were collected by venipuncture from a peripheral vein from restrained, conscious animals.

Knockdown of TTR was observed in all treated groups with observation at Days 10 and 20 after dosing. The study period was lengthened to 50 days for one group to observe long-term effects.

Figure 11:
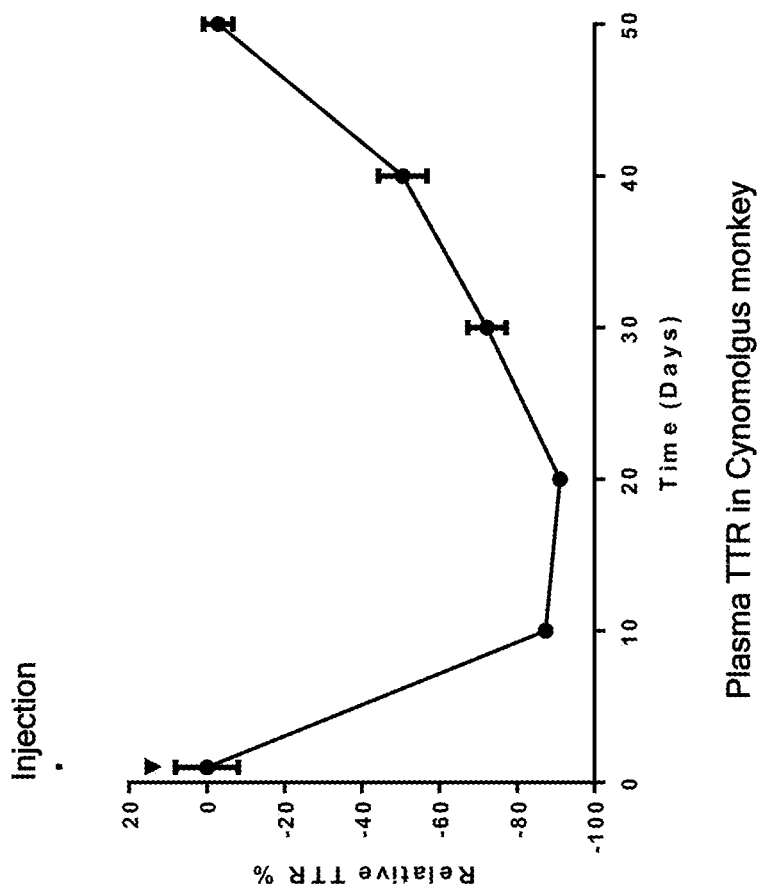
FIG. 11 shows knockdown of Transthyretin protein in vivo as a result of treatment with UNA oligomers targeting Transthyretin TTR mRNA, delivered in a liposomal formulation to male Cynomolgus monkeys. Measurements were made following a single intravenous (IV) dose administration. TTR protein concentration in plasma samples was assessed by LC-MS/MS at various time points. Animals were administered test doses on Day 1 at 0.3 mg/kg. Doses were administered as a 15-minute intravenous (IV) infusion, ±1 minute, using a pump and disposable syringe.

Referring to FIG. 11, knockdown of Transthyretin protein in vivo was achieved as a result of treatment with UNA oligomer SEQ ID NO:60/100 targeting Transthyretin TTR mRNA, delivered in a liposomal formulation to male Cynomolgus monkeys. Measurements were made following a single intravenous (IV) dose administration. TTR protein concentration in plasma samples was assessed by LC-MS/MS at various time points.

As shown in FIG. 11, a single injection in the primates of a UNA oligomer targeted to TTR surprisingly knocked down TTR protein levels to below 50% with a continuous duration of more than one month (30 days).

FIG. 11 shows the unexpectedly advantageous result of over 91% knockdown of TTR in the primates at 20 days, and more than 70% knockdown with a continuous duration of more than 20 days.

The Monkey TTR SRM assay was used, which is a high throughput absolute protein quantitation assay using Selected Reaction Monitoring (SRM) technology platform. In a single SRM assay, the panel can multiplex up to 200 proteins. The assay was performed on a targeted absolute protein quantitation platform, where the key technology was SRM, sometimes also referred to as Multiple Reaction Monitoring (MRM). In a triple-quadrupole (QQQ) mass spectrometer, SRM/MRM is a tandem selection process where selecting peptides by precursor m/z is followed by selecting fragmentations (transitions) of the targeted peptide. Further, coupled with liquid chromatography and the addition of heavy labeled internal standards, SRM/MRM is a highly selective, sensitive technology to quantify designated protein with precision.

All publications, patents and literature specifically mentioned herein are incorporated by reference for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be encompassed by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

---

What is claimed is:

1. A composition comprising:
   i) a compound comprising a first strand and a second strand, each of the strands being 19-29 monomers in length, the monomers comprising UNA monomers and nucleic acid monomers, wherein the compound has a duplex region of from 14 to 29 contiguous monomers in length, wherein the first strand is a passenger strand for RNA interference and the second strand is a guide strand for RNA interference, and wherein the compound comprises a sequence of bases targeted to inhibit expression of a TTR gene; and
   ii) a carrier comprising lipid nanoparticles or liposomes, wherein the lipid nanoparticles or liposomes comprise one or more of the compounds selected from ATX-001 to ATX-032.

2. The composition of claim 1, wherein the compound contains one to seven UNA monomers.

3. The composition of claim 1, wherein the compound contains a UNA monomer at the 1-end (5' end for non-UNA) of the first strand, a UNA monomer at the second position from the 3' end of the first strand, and a UNA monomer at the second position from the 3' end of the second strand.

4. The composition of claim 1, wherein the compound contains a UNA monomer at any one or more of positions 2 to 8 from the 5' end of the second strand.

5. The composition of claim 1, wherein the compound comprises SEQ ID NOs:60/100, SEQ ID NOs:59/99, SEQ ID NOs:43/83, or SEQ ID NOs:61/101.

6. The composition of claim 1, wherein the compound has a 3' overhang comprising one or more UNA monomers, natural nucleotides, non-natural nucleotides, modified nucleotides, or chemically-modified nucleotides, or combinations thereof.

7. The composition of claim 1, wherein one or more of the nucleic acid monomers is a non-natural nucleotide, a modified nucleotide, or a chemically-modified nucleotide.

8. The composition of claim 1, wherein one or more of the nucleic acid monomers has a $2^1$-0-methyl group.

9. The composition of claim 1, wherein one or more of three monomers at each end of each strand is connected by a phosphorothioate, a chiral phosphorothioate, or a phosphorodithioate linkage.

10. The composition of claim 1, wherein upon administering a single intravenous dose to a subject, the composition reduces TTR protein in the subject by at least 50% after 30 days.

11. A method for treating TTR-related amyloidosis in a subject in need, the method comprising administering to the subject an effective amount of a composition of claim 1 to the subject.

12. The method of claim 11, wherein the TTR-related amyloidosis is ATTR.

13. The method of claim 11, wherein the administering is intravenous, subcutaneous, pulmonary, intramuscular, intraperitoneal, or dermal.

14. The method of claim 11, wherein the effective amount is a dose of from 0.001 to 10.0 mg/kg.

15. The method of claim 11, wherein upon administering a single dose to the subject, the composition reduces TTR protein in the subject by at least 50% after 30 days.

16. A method for inhibiting expression of a TTR gene in a subject, the method comprising administering to the subject a composition of claim 1.

* * * * *

SEQUENCE LISTING

```
<160> NUMBER OF SEQ ID NOS: 146

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 1
nnnnnnnnnn nnnnnnnnnn nn                                              22

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 2
nnnnnnnnnn nnnnnnnnnn n                                               21

<210> SEQ ID NO 3
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 3
ggccaugcau guguucagau u                                              21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ucugaacaca ugcauggccu u                                              21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ggccaugcau guguucagau u                                              21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ucugaacaca ugcauggccu u                                              21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ggccaugcau guguucagau u                                              21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ucugaacaca ugcauggccu u                                              21

<210> SEQ ID NO 9
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 9
ggccaugcau guguucagau u                                              21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
ucugaacaca ugcauggccu u                                              21

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ggccaugcau guguucagau u                                              21

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ucugaacaca ugcauggccu u                                              21

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gccaugcaug uguucagaau u                                              21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uucugaacac augcauggcu u                                              21

<210> SEQ ID NO 15
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 15
gccaugcaug uguucagaau u                                                  21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uucugaacac augcauggcu u                                                  21

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gccaugcaug uguucagaau u                                                  21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
uucugaacac augcauggcu u                                                  21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gccaugcaug uguucagaau u                                                  21

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uucugaacac augcauggcu u                                                  21

<210> SEQ ID NO 21
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 21
gccaugcaug uguucagaau u                                              21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uucugaacac augcauggcu u                                              21

<210> SEQ ID NO 23
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
auguaaccaa gaguauucca uuuuuac                                        27

<210> SEQ ID NO 24
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
auguaaccaa gaguauucca uuuuuac                                        27

<210> SEQ ID NO 25
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
auguaaccaa gaguauucca uuuuuac                                        27

<210> SEQ ID NO 26
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
auguaaccaa gaguauucca uuuuuac                                        27

<210> SEQ ID NO 27
<211> LENGTH: 27
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 27
auguaaccaa gaguauucca uuuuuac                                              27

<210> SEQ ID NO 28
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
auguaaccaa gaguauucca uuuuuac                                              27

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 29
guaaccaaga guauuccauu uuuacta                                              27

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 30
guaaccaaga guauuccauu uuuacta                                              27

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
guaaccaaga guauuccauu uuuacta                                              27

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<220> FEATURE:
<223> OTHER INFORMATION: Description of Combined DNA/RNA Molecule:
      Synthetic oligonucleotide

<400> SEQUENCE: 32
guaaccaaga guauuccauu uuuacta                                            27

<210> SEQ ID NO 33
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
guaaccaaga guauuccauu uuuacua                                            27

<210> SEQ ID NO 34
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
guaaccaaga guauuccauu uuuacua                                            27

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 35
guaaccaaga guauuccaut t                                                  21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36
guaaccaaga guauuccaut t                                                  21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 37
guaaccaaga guauuccaut t                                              21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
guaaccaaga guauuccauu u                                              21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
guaaccaaga guauuccauu u                                              21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
guaaccaaga guauuccauu u                                              21

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
guaaccaaga guauuccauu u                                              21

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
guaaccaaga guauuccauu u                                              21

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 43
guaaccaaga guauuccauu u                                              21

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
guaaccaaga guauuccauu u                                              21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
guaaccaaga guauuccauu u                                              21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
guaaccaaga guauuccauu u                                              21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
auguaaccaa gaguauuccu u                                              21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
auguaaccaa gaguauuccu u                                              21

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 49
auguaaccaa gaguauuccu u                                              21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
auguaaccaa gaguauuccu u                                              21

<210> SEQ ID NO 51
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
agaguauucc auuuuuacuu                                                20

<210> SEQ ID NO 52
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
agaguauucc auuuuuacuu                                                20

<210> SEQ ID NO 53
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
agaguauucc auuuuuacuu                                                20

<210> SEQ ID NO 54
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
agaguauucc auuuuuacuu                                                20

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 55
gacugguauu ugugucugau u                                              21

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
gacugguauu ugugucugau u                                              21

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
gacugguauu ugugucugau u                                              21

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
gacugguauu ugugucugau u                                              21

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
uguaaccaag aguauuccau u                                              21

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
uaaccaagag uauuccauuu u                                              21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 61
ccaagaguau uccauuuuuu u                                              21

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
ccaagaguau uccauuuuuu u                                              21

<210> SEQ ID NO 63
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
guaaaaaugg aauacucuug guuacau                                        27

<210> SEQ ID NO 64
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
guaaaaaugg aauacucuug guuacau                                        27

<210> SEQ ID NO 65
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
guaaaaaugg aauacucuug guuacau                                        27

<210> SEQ ID NO 66
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
guaaaaaugg aauacucuug guuacau                                        27

<210> SEQ ID NO 67
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 67
guaaaaaugg aauacucuug guuacau                                          27

<210> SEQ ID NO 68
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
guaaaaaugg aauacucuug guuacau                                          27

<210> SEQ ID NO 69
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
uaguaaaaau ggaauacucu ugguuac                                          27

<210> SEQ ID NO 70
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
uaguaaaaau ggaauacucu ugguuac                                          27

<210> SEQ ID NO 71
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
uaguaaaaau ggaauacucu ugguuac                                          27

<210> SEQ ID NO 72
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
uaguaaaaau ggaauacucu ugguuac                                          27

<210> SEQ ID NO 73
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 73
uaguaaaaau ggaauacucu ugguuac                                           27

<210> SEQ ID NO 74
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
uaguaaaaau ggaauacucu ugguuac                                           27

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 75
auggaauacu cuugguuact t                                                 21

<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
auggaauacu cuugguuacu u                                                 21

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
auggaauacu cuugguuacu u                                                 21

<210> SEQ ID NO 78
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
auggaauacu cuugguuacu u                                                 21

<210> SEQ ID NO 79
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 79
auggaauacu cuugguuacu u                                              21

<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
auggaauacu cuugguuacu u                                              21

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
auggaauacu cuugguuacu u                                              21

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
auggaauacu cuugguuaca u                                              21

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
auggaauacu cuugguuacu u                                              21

<210> SEQ ID NO 84
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
auggaauacu cuugguuacu u                                              21

<210> SEQ ID NO 85
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 85
auggaauacu cuugguuacu u                                              21

<210> SEQ ID NO 86
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
auggaauacu cuugguuacu u                                              21

<210> SEQ ID NO 87
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
ggaauacucu ugguuacauu u                                              21

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
ggaauacucu ugguuacauu u                                              21

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
ggaauacucu ugguuacauu u                                              21

<210> SEQ ID NO 90
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
ggaauacucu ugguuacauu u                                              21

<210> SEQ ID NO 91
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 91
aguaaaaaug gaauacucuu                                                    20

<210> SEQ ID NO 92
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
aguaaaaaug gaauacucuu                                                    20

<210> SEQ ID NO 93
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
aguaaaaaug gaauacucuu                                                    20

<210> SEQ ID NO 94
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
aguaaaaaug gaauacucuu                                                    20

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
ucagacacaa auaccagucc a                                                  21

<210> SEQ ID NO 96
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
ucagacacaa auaccagucc a                                                  21

<210> SEQ ID NO 97
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 97
ucagacacaa auaccagucc a                                                    21

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
ucagacacaa auaccagucc a                                                    21

<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
uggaauacuc uugguuacau u                                                    21

<210> SEQ ID NO 100
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
aauggaauac ucuugguuau u                                                    21

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
aaaaauggaa uacucuuggu u                                                    21

<210> SEQ ID NO 102
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
aaaaauggaa uacucuuggu u                                                    21

<210> SEQ ID NO 103
<211> LENGTH: 41
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 103
guccugccau caauguggcc augcaugugu ucagaaaggc u                     41

<210> SEQ ID NO 104
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
guccugccau caauguggcc gugcaugugu ucagaaaggc u                     41

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 105
acggccacau ugauggcagt t                                           21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 106
cacggccaca uugauggcat t                                           21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 107
gcacggccac auugauggct t                                           21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 108
ugcacggcca cauugauggt t                                              21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 109
augcacggcc acauugaugt t                                              21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 110
caugcacggc cacauugaut t                                              21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 111
acaugcacgg ccacauugat t                                              21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 112
cacaugcacg gccacauugt t                                              21

<210> SEQ ID NO 113
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 113
acacaugcac ggccacauut t                                              21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 114
aacacaugca cggccacaut t                                              21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 115
gaacacaugc acggccacat t                                              21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 116
ugaacacaug cacggccact t                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117
cugaacacau gcacggccat t                                              21
```

```
<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 118
ucugaacaca ugcacggcct t                                              21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 119
ugcauggcca cauugauggt t                                              21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 120
cacaugcaug gccacauugt t                                              21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 121
cugaacacau gcauggccat t                                              21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 122
ucugaacaca ugcauggcct t                                              21
```

```
<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 123
ggccaugcau guguucagat t                                             21

<210> SEQ ID NO 124
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
ggccaugcau guguucagau u                                             21

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
ggccaugcau guguucagau u                                             21

<210> SEQ ID NO 126
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
ggccaugcau guguucagau u                                             21

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
ggccaugcau guguucagau u                                             21

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
ggccaugcau guguucagau u                                             21
```

```
<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 129
ucugaacaca ugcauggcct t                                              21

<210> SEQ ID NO 130
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
ucugaacaca ugcauggccu u                                              21

<210> SEQ ID NO 131
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
ucugaacaca ugcauggccu u                                              21

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
ucugaacaca ugcauggccu u                                              21

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
ucugaacaca ugcauggccu u                                              21

<210> SEQ ID NO 134
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
ucugaacaca ugcauggccu u                                              21
```

```
<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 135
gccaugcaug uguucagaat t                                              21

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
gccaugcaug uguucagaau u                                              21

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
gccaugcaug uguucagaau u                                              21

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
gccaugcaug uguucagaau u                                              21

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
gccaugcaug uguucagaau u                                              21

<210> SEQ ID NO 140
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
gccaugcaug uguucagaau u                                              21
```

```
<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 141
uucugaacac augcauggct t                                              21

<210> SEQ ID NO 142
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
uucugaacac augcauggcu u                                              21

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
uucugaacac augcauggcu u                                              21

<210> SEQ ID NO 144
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
uucugaacac augcauggcu u                                              21

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
uucugaacac augcauggcu u                                              21

<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 146
uucugaacac augcauggcu u                                          21
```